(12) United States Patent
Nakamura et al.

(10) Patent No.: US 7,897,329 B2
(45) Date of Patent: Mar. 1, 2011

(54) **METHOD FOR DIAGNOSING NON-SMALL CELL LUNG CANCERS BY TRNA-DIHYDROURIDINE SYNTHASE ACTIVITY OF *URLC8***

(75) Inventors: Yusuke Nakamura, Bunkyo-ku (JP); Yataro Daigo, Bunkyo-ku (JP); Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 258 days.

(21) Appl. No.: 11/575,812

(22) PCT Filed: Sep. 21, 2005

(86) PCT No.: PCT/JP2005/017915

§ 371 (c)(1),
(2), (4) Date: Oct. 8, 2007

(87) PCT Pub. No.: WO2006/033460

PCT Pub. Date: Mar. 30, 2006

(65) Prior Publication Data

US 2008/0119428 A1 May 22, 2008

Related U.S. Application Data

(60) Provisional application No. 60/612,937, filed on Sep. 24, 2004.

(51) Int. Cl.
*C12Q 1/00* (2006.01)
*G01N 33/574* (2006.01)
(52) U.S. Cl. .............................. 435/4; 435/7.23; 435/7.1
(58) Field of Classification Search ........................ None
See application file for complete search history.

(56) References Cited

U.S. PATENT DOCUMENTS

| | | |
|---|---|---|
| 2003/0228618 A1 | 12/2003 | Levanon et al. |
| 2004/0142325 A1 | 7/2004 | Mintz et al. |
| 2006/0024692 A1 | 2/2006 | Nakamura et al. |
| 2007/0224201 A1* | 9/2007 | Wu et al. ................. 424/155.1 |

FOREIGN PATENT DOCUMENTS

| | | | |
|---|---|---|---|
| WO | WO 00/78954 A | | 12/2000 |
| WO | WO0078954 | * | 12/2000 |
| WO | WO0153312 | * | 7/2001 |
| WO | WO 01/75067 A | | 10/2001 |
| WO | WO 2004/030615 A | | 4/2004 |
| WO | WO 2004/031413 A | | 4/2004 |

OTHER PUBLICATIONS

Wu et al., WO 2004/030615, published Apr. 15, 2004, pp. 245-246,381-385.*
Sequence seach result, 2009.*
Dalluge, J. et al., "Conformational flexibility in RNA: the role of dihydrouridine," *Nucleic Acids Research*, vol. 24(6): 1073-1079 (Mar. 1996).
Hunninghake, D. and S. Grisolia. "A sensitive and convenient micromethod for estimation of urea, citrulline and carbamyl derivatives," *Analytical Biochemistry*, vol. 16(2): 200-205 (Aug. 1966).
Jacobson, M. and C. Hedgcoth. "Determination of 5,6-dihydrouridine in ribonucleic acid," *Analytical Biochemistry*, vol. 34(2): 459-469 (Apr. 1970).
Kato, T., et al. Isolation and characterization of a novel gene IMS-E21 as a therapeutic target for non-small cell lung cancer [Abstract]. In: Proceedings of the 95th Annual Meeting of the American Association for Cancer Research: Mar. 27-31, 2004; Orlando, FL. Philadelphia (PA): AACR: 2004. vol. 45; p. 799; Abstract #3459.
Kato, T., et al. Isolation and characterization of a novel gene IMS-E21 as a therapeutic target for non-small cell lung cancer [Abstract]. In: Program of the Sixty-Third Annual Meeting of the Japanese Cancer Association; Sep. 29-Oct. 1, 2004; Fukuoka, Japan. Cancer Science 2004 vol. 95 Supplement (August); p. 54; Abstract # W-070.
Kato, T., et al. Isolation and characterization of a novel gene *IMS-E21* as a therapeutic target for non-small cell lung cancer [Abstract]. In: Proceedings of the 96th Annual Meeting of the American Association for Cancer Research; Apr. 16-20, 2005; Anaheim, CA. Philadelphia (PA): AACR: 2005. vol. 46; p. 857; Abstract #3635.
Kato, T., et al. A novel human tRNA-dihydrouridine synthase involved in pulmonary carcinogenesis [Abstract]. In: Proceedings of the Sixty-Fourth Annual Meeting of the Japanese Cancer Association; Sep. 14-16, 2005; Sapporo, Japan. JCA: 2005 (August); p. 240; Abstract #W-345.
Kuchino, Y. and E. Borek. "Tumour-specific phenylalanine tRNA contains two supernumerary methylated bases," *Nature*, vol. 271: 126-129 (Jan. 1978).
Kato, T., et al., "A novel human tRNA-dihydrouridine synthase involved in pulmonary carcinogenesis," *Cancer Research*, vol. 65(13): 5638-5646 (Jul. 2005).
Kikuchi, T., et al., "Expression profiles of non-small cell lung cancers on cDNA microarrays: Identification of genes for prediction of lymph-node metastasis and sensitivity to anti-cancer drugs," *Oncogene*, vol. 22: 2192-2205 (2003).
Suzuki, C., et al., "Identification of COX17 as a therapeutic target for non-small cell lung cancer," *Cancer Research*, vol. 63: 7038-7041 (Nov. 2003).
Xing, F., et al., "A conserved family of *Saccharomyces cerevisiae* synthases effects dihydrouridine modification of tRNA," *RNA*, vol. 8(3): 370-381 (Mar. 2002).

*Primary Examiner*—Larry R. Helms
*Assistant Examiner*—Lei Yao
(74) *Attorney, Agent, or Firm*—Townsend and Townsend and Crew LLP

(57) ABSTRACT

The present invention features a method for determining t-RNA dihydrouridine-synthase activity of a polypeptide and screening for modulators of t-RNA dihydrouridine-synthase activity. The present invention further provides methods or pharmaceutical compositions for preventing and/or treating non-small cell lung cancer (NSCLC) using such modulators. Furthermore, the present invention provides methods for diagnosing non-small cell lung cancer (NSCLC) using the t-RNA dihydrouridine-synthase activity of IMS-E21 (URLC8) protein as an index. The present invention further provides methods for predicting and prognosing lung squamous-cell carcinoma (SCC).

1 Claim, 7 Drawing Sheets

OTHER PUBLICATIONS

Oue, et al., "Expression and Localization of Reg IV in Human Neoplastic and Non-Neoplastic Tissues: Reg IV Expression is Associated with Intestinal and Neuroendocrine Differentiation in Gastric Adencarcinoma," *Journal of Pathology,* 2005, 207, pp. 185-198.

Takehara, et al., "Novel Tumor Marker REG4 Detected in Serum of Patients with Resectable Pancreatic Cancer and Feasibility for Antibody Therapy Targeting REG4," *Cancer Sci,* Nov. 2006, vol. 97, No. 11, pp. 1191-1197.

* cited by examiner

Continuation of Fig. 1 b

| | | 10 | 20 | 30 | 40 | 50 |
|---|---|---|---|---|---|---|
| IMS-E21 (H.sapiens) | 1 | M- | ------ | ------ | ------ | ------ |
| 2310016K04Rik (Mus musculus) | 1 | M- | ------ | ------ | ------ | ------ |
| LOC291978 (R. norvegicus) | 1 | M- | ------ | ------ | ------ | ------ |
| CG1434-PA (D. melanogaster) | 1 | M----- | -LRLP | TILRKSFSMK | ------ | ------ |
| Y54E5A.6 (C. elegans) | 1 | MSDL- | ------ | ------ | ------ | ------ |
| Dus2 (S. cerevisiae) | 1 | M----- | ------ | ------ | ------ | ------ |
| Dus1 (S. cerevisiae) | 1 | MTEPALSSAN | NALMQKLTGR | QLFDKIGRPT | ------ | ------ |

(sequence alignment figure; continuation of Fig. 1)

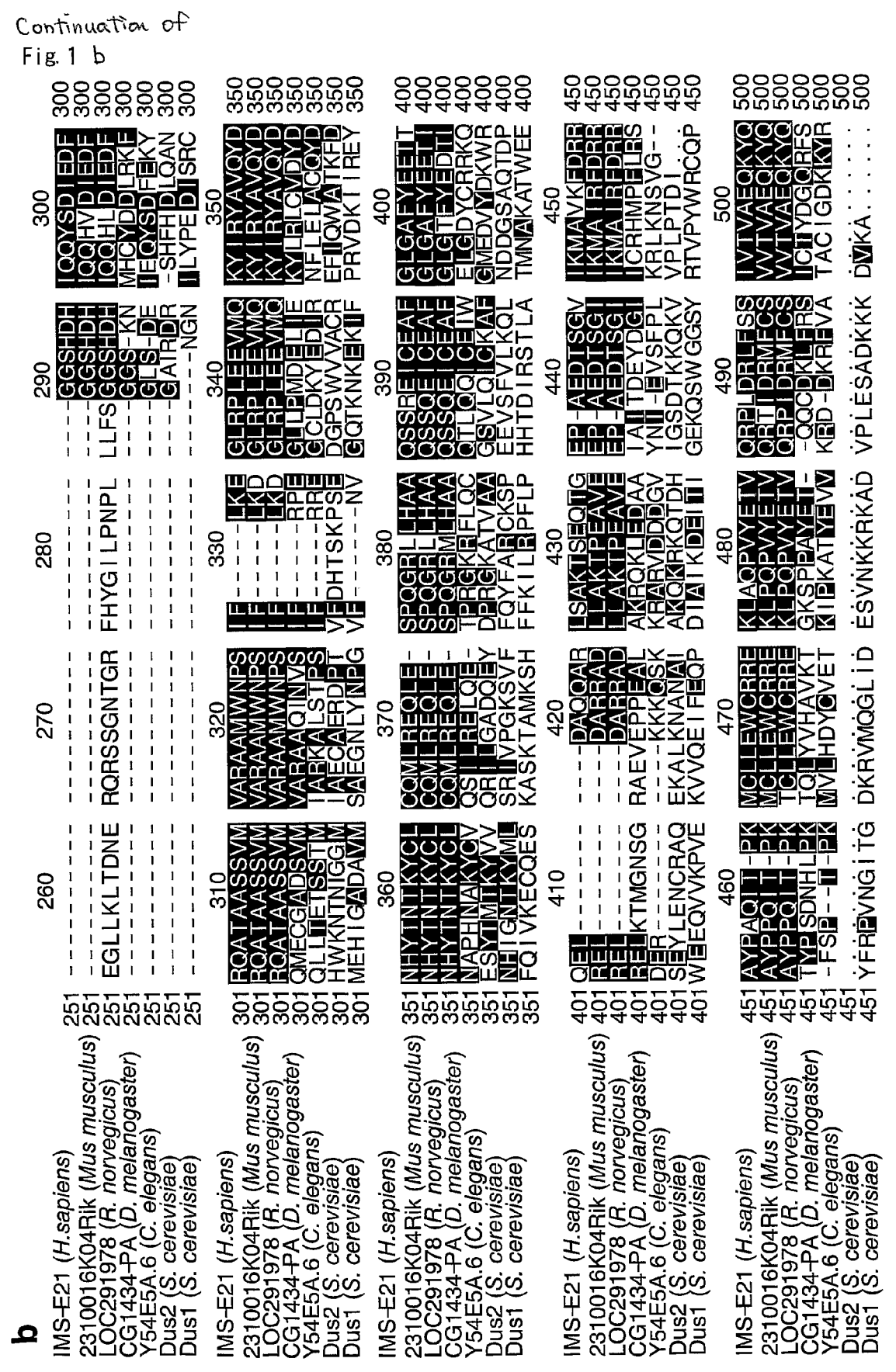

Continuation of Fig. 1 b

Continuation of Fig. 1b

| | | 510 | 520 | 530 | 540 | 550 | |
|---|---|---|---|---|---|---|---|
| IMS-E21 (H.sapiens) | 501 | STLWDKSKKL | AEQAAAIVCL | RSQGLPEGRL | GEEESPSLHKR | KREAPDQDPG | 550 |
| 2310016K04Rik (Mus musculus) | 501 | STLWDKSKKL | AEQTAAIVCL | RSQGLPEGRL | GEEESPSLNKR | KREAPDQDPG | 550 |
| LOC291978 (R. norvegicus) | 501 | STLWDKSKKL | AEQTAAIVCL | RSQGLPEGRL | GEEENPSLNKR | KREAPNQDPG | 550 |
| CG1434-PA (D. melanogaster) | 501 | SSFWEKNKKQ | AEQGAALVAL | LHLGQLEAEV | LRDNGISLLN. | .......... | 550 |
| Y54E5A.6 (C. elegans) | 501 | SGIGQPNLRM | AEQVAALAAL | HGMNIRNLLV | GNWEEE..... | .......... | 550 |
| Dus2 (S. cerevisiae) | 501 | .......... | .......... | .......... | .......... | .......... | 550 |
| Dus1 (S. cerevisiae) | 501 | .......... | .......... | .......... | .......... | .......... | 550 |

| | | 560 | 570 | 580 | 590 | 600 | |
|---|---|---|---|---|---|---|---|
| IMS-E21 (H.sapiens) | 551 | GPRAQELAQP | GDLCKKPFVA | LGSGEESPLE | GW........ | .......... | 600 |
| 2310016K04Rik (Mus musculus) | 551 | GPRVQEPALP | GEICKKPFVI | LDSSEENLLE | GC........ | .......... | 600 |
| LOC291978 (R. norvegicus) | 551 | GPRVQETALP | GEICKKPFVT | LESSEENLLE | GC........ | .......... | 600 |
| CG1434-PA (D. melanogaster) | 551 | .......... | .......... | .......... | .......... | .......... | 600 |
| Y54E5A.6 (C. elegans) | 551 | .......... | .......... | .......... | .......... | .......... | 600 |
| Dus2 (S. cerevisiae) | 551 | .......... | .......... | .......... | .......... | .......... | 600 |
| Dus1 (S. cerevisiae) | 551 | .......... | .......... | .......... | .......... | .......... | 600 | a  Clinical sample

Adenocarcinoma

Squamous-Cell Carcinoma b  Lung cancer cell line c

SEQUENCE LISTING

```
<160> NUMBER OF SEQ ID NOS: 33

<210> SEQ ID NO 1
<211> LENGTH: 2020
<212> TYPE: DNA
<213> ORGANISM: Homo sapiens
<220> FEATURE:
<221> NAME/KEY: CDS
<222> LOCATION: (171)...(1652)

<400> SEQUENCE: 1
gctcagtacg gtgtgtggag ctggagcacc gtgaggaaga agcgaggttc tttttaagag      60
ttcagctgcg agatatcaaa caaagaatta ctctgtacaa agccagaaca catatatcaa     120
agtaatcctg aagtatcaga acaaaataat aggctgtaac agaggaggaa atg att        176
                                                         Met Ile
```

```
                                     1
ttg aat agc ctc tct ctg tgt tac cat aat aag cta atc ctg gcc cca      224
Leu Asn Ser Leu Ser Leu Cys Tyr His Asn Lys Leu Ile Leu Ala Pro
          5                  10                  15 atg gtt cgg gta ggg act ctt cca atg agg ctg ctg gcc ctg gat tat      272
Met Val Arg Val Gly Thr Leu Pro Met Arg Leu Leu Ala Leu Asp Tyr
 20                  25                  30 gga gcg gac att gtt tac tgt gag gag ctg atc gac ctc aag atg att      320
Gly Ala Asp Ile Val Tyr Cys Glu Glu Leu Ile Asp Leu Lys Met Ile
 35                  40                  45                  50 cag tgc aag aga gtt gtt aat gag gtg ctc agc aca gtg gac ttt gtc      368
Gln Cys Lys Arg Val Val Asn Glu Val Leu Ser Thr Val Asp Phe Val
                 55                  60                  65 gcc cct gat gat cga gtt gtc ttc cgc acc tgt gaa aga gag cag aac      416
Ala Pro Asp Asp Arg Val Val Phe Arg Thr Cys Glu Arg Glu Gln Asn
         70                  75                  80 agg gtg gtc ttc cag atg ggg act tca gac gca gag cga gcc ctt gct      464
Arg Val Val Phe Gln Met Gly Thr Ser Asp Ala Glu Arg Ala Leu Ala
             85                  90                  95 gtg gcc agg ctt gta gaa aat gat gtg gct ggt att gat gtc aac atg      512
Val Ala Arg Leu Val Glu Asn Asp Val Ala Gly Ile Asp Val Asn Met
100                 105                 110 ggc tgt cca aaa caa tat tcc acc aag gga gga atg gga gct gcc ctg      560
Gly Cys Pro Lys Gln Tyr Ser Thr Lys Gly Gly Met Gly Ala Ala Leu
115                 120                 125                 130 ctg tca gac cct gac aag att gag aag atc ctc agc act ctt gtt aaa      608
Leu Ser Asp Pro Asp Lys Ile Glu Lys Ile Leu Ser Thr Leu Val Lys
                135                 140                 145 ggg aca cgc aga cct gtg acc tgc aag att cgc atc ctg cca tcg cta      656
Gly Thr Arg Arg Pro Val Thr Cys Lys Ile Arg Ile Leu Pro Ser Leu
            150                 155                 160 gaa gat acc ctg agc ctt gtg aag cgg ata gag agg act ggc att gct      704
Glu Asp Thr Leu Ser Leu Val Lys Arg Ile Glu Arg Thr Gly Ile Ala
        165                 170                 175 gcc atc gca gtt cat ggg agg aag cgg gag gag cga cct cag cat cct      752
Ala Ile Ala Val His Gly Arg Lys Arg Glu Glu Arg Pro Gln His Pro
180                 185                 190 gtc agc tgt gaa gtc atc aaa gcc att gct gat acc ctc tcc att cct      800
Val Ser Cys Glu Val Ile Lys Ala Ile Ala Asp Thr Leu Ser Ile Pro
195                 200                 205                 210 gtc ata gcc aac gga gga tct cat gac cac atc caa cag tat tcg gac      848
Val Ile Ala Asn Gly Gly Ser His Asp His Ile Gln Gln Tyr Ser Asp
                215                 220                 225 ata gag gac ttt cga caa gcc acg gca gcc tct tcc gtg atg gtg gcc      896
Ile Glu Asp Phe Arg Gln Ala Thr Ala Ala Ser Ser Val Met Val Ala
            230                 235                 240 cga gca gcc atg tgg aac cca tct atc ttc ctc aag gag ggt ctg cgg      944
Arg Ala Ala Met Trp Asn Pro Ser Ile Phe Leu Lys Glu Gly Leu Arg
        245                 250                 255 ccc ctg gag gag gtc atg cag aaa tac atc aga tac gcg gtg cag tat      992
Pro Leu Glu Glu Val Met Gln Lys Tyr Ile Arg Tyr Ala Val Gln Tyr
260                 265                 270 gac aac cac tac acc aac acc aag tac tgc ttg tgc cag atg cta cga     1040
Asp Asn His Tyr Thr Asn Thr Lys Tyr Cys Leu Cys Gln Met Leu Arg
275                 280                 285                 290 gaa cag ctg gag tcg ccc cag gga agg ttg ctc cat gct gcc cag tct     1088
Glu Gln Leu Glu Ser Pro Gln Gly Arg Leu Leu His Ala Ala Gln Ser
                295                 300                 305 tcc cgg gaa att tgt gag gcc ttt ggc ctt ggt gcc ttc tat gag gag     1136
```

```
                Ser Arg Glu Ile Cys Glu Ala Phe Gly Leu Gly Ala Phe Tyr Glu Glu
                            310                 315                 320 acc aca cag gag ctg gat gcc cag cag gcc agg ctc tca gcc aag act            1184
Thr Thr Gln Glu Leu Asp Ala Gln Gln Ala Arg Leu Ser Ala Lys Thr
            325                 330                 335 tca gag cag aca ggg gag cca gct gaa gat acc tct ggt gtc att aag            1232
Ser Glu Gln Thr Gly Glu Pro Ala Glu Asp Thr Ser Gly Val Ile Lys
        340                 345                 350 atg gct gtc aag ttt gac cgg aga gca tac cca gcc cag atc acc cct            1280
Met Ala Val Lys Phe Asp Arg Arg Ala Tyr Pro Ala Gln Ile Thr Pro
355                 360                 365                 370 aag atg tgc cta cta gag tgg tgc cgg agg gag aag ttg gca cag cct            1328
Lys Met Cys Leu Leu Glu Trp Cys Arg Arg Glu Lys Leu Ala Gln Pro
                375                 380                 385 gtg tat gaa acg gtt caa cgc cct cta gat cgc ctg ttc tcc tct att            1376
Val Tyr Glu Thr Val Gln Arg Pro Leu Asp Arg Leu Phe Ser Ser Ile
            390                 395                 400 gtc acc gtt gct gaa caa aag tat cag tct acc ttg tgg gac aag tcc            1424
Val Thr Val Ala Glu Gln Lys Tyr Gln Ser Thr Leu Trp Asp Lys Ser
        405                 410                 415 aag aaa ctg gcg gag cag gct gca gcc atc gtc tgt ctg cgg agc cag            1472
Lys Lys Leu Ala Glu Gln Ala Ala Ala Ile Val Cys Leu Arg Ser Gln
420                 425                 430 ggc ctc cct gag ggt cgg ctg ggt gag gag agc cct tcc ttg cac aag            1520
Gly Leu Pro Glu Gly Arg Leu Gly Glu Glu Ser Pro Ser Leu His Lys
435                 440                 445                 450 cga aag agg gag gct cct gac caa gac cct ggg ggc ccc aga gct cag            1568
Arg Lys Arg Glu Ala Pro Asp Gln Asp Pro Gly Gly Pro Arg Ala Gln
                455                 460                 465 gag cta gca caa cct ggg gat ctg tgc aag aag ccc ttt gtg gcc ttg            1616
Glu Leu Ala Gln Pro Gly Asp Leu Cys Lys Lys Pro Phe Val Ala Leu
            470                 475                 480 gga agt ggt gaa gaa agc ccc ctg gaa ggc tgg tga ctactcttcc                 1662
Gly Ser Gly Glu Glu Ser Pro Leu Glu Gly Trp
        485                 490 tgccttagtc accccctccat gggcctggtg ctaaggtggc tgtggatgcc acagcatgaa         1722
ccagatgccg ttgaacagtt tgctggtctt gcctggcaga agttagatgt cctggcaggg         1782
gccatcagcc tagagcatgg accaggggcc gcccaggggt ggatcctggc ccctttggtg         1842
gatctgagtg acagggtcaa gttctctttg aaaacaggag cttttcaggt ggtaactccc         1902
caacctgaca ttggtactgt gcaataaaga caccccctac cctcaaaaaa aaaaaaaaaa         1962
aaaaaaaaaa aaaaaaaaaa aaaaaaaaaa aaaaaaaaaa aaaaaaaaaa aaaaaaa            2020

<210> SEQ ID NO 2
<211> LENGTH: 493
<212> TYPE: PRT
<213> ORGANISM: Homo sapiens

<400> SEQUENCE: 2

Met Ile Leu Asn Ser Leu Ser Leu Cys Tyr His Asn Lys Leu Ile Leu
1               5                   10                  15

Ala Pro Met Val Arg Val Gly Thr Leu Pro Met Arg Leu Leu Ala Leu
            20                  25                  30

Asp Tyr Gly Ala Asp Ile Val Tyr Cys Glu Glu Leu Ile Asp Leu Lys
        35                  40                  45

Met Ile Gln Cys Lys Arg Val Val Asn Glu Val Leu Ser Thr Val Asp
    50                  55                  60
```

```
Phe Val Ala Pro Asp Asp Arg Val Val Phe Arg Thr Cys Glu Arg Glu
 65                  70                  75                  80

Gln Asn Arg Val Val Phe Gln Met Gly Thr Ser Asp Ala Glu Arg Ala
                 85                  90                  95

Leu Ala Val Ala Arg Leu Val Glu Asn Asp Val Ala Gly Ile Asp Val
            100                 105                 110

Asn Met Gly Cys Pro Lys Gln Tyr Ser Thr Lys Gly Gly Met Gly Ala
            115                 120                 125

Ala Leu Leu Ser Asp Pro Asp Lys Ile Glu Lys Ile Leu Ser Thr Leu
130                 135                 140

Val Lys Gly Thr Arg Arg Pro Val Thr Cys Lys Ile Arg Ile Leu Pro
145                 150                 155                 160

Ser Leu Glu Asp Thr Leu Ser Leu Val Lys Arg Ile Glu Arg Thr Gly
                165                 170                 175

Ile Ala Ala Ile Ala Val His Gly Arg Lys Arg Glu Glu Arg Pro Gln
            180                 185                 190

His Pro Val Ser Cys Glu Val Ile Lys Ala Ile Ala Asp Thr Leu Ser
            195                 200                 205

Ile Pro Val Ile Ala Asn Gly Gly Ser His Asp His Ile Gln Gln Tyr
            210                 215                 220

Ser Asp Ile Glu Asp Phe Arg Gln Ala Thr Ala Ala Ser Ser Val Met
225                 230                 235                 240

Val Ala Arg Ala Ala Met Trp Asn Pro Ser Ile Phe Leu Lys Glu Gly
                245                 250                 255

Leu Arg Pro Leu Glu Glu Val Met Gln Lys Tyr Ile Arg Tyr Ala Val
            260                 265                 270

Gln Tyr Asp Asn His Tyr Thr Asn Thr Lys Tyr Cys Leu Cys Gln Met
            275                 280                 285

Leu Arg Glu Gln Leu Glu Ser Pro Gln Gly Arg Leu Leu His Ala Ala
            290                 295                 300

Gln Ser Ser Arg Glu Ile Cys Glu Ala Phe Gly Leu Gly Ala Phe Tyr
305                 310                 315                 320

Glu Glu Thr Thr Gln Glu Leu Asp Ala Gln Ala Arg Leu Ser Ala
                325                 330                 335

Lys Thr Ser Glu Gln Thr Gly Pro Ala Glu Asp Thr Ser Gly Val
            340                 345                 350

Ile Lys Met Ala Val Lys Phe Asp Arg Arg Ala Tyr Pro Ala Gln Ile
            355                 360                 365

Thr Pro Lys Met Cys Leu Leu Glu Trp Cys Arg Arg Glu Lys Leu Ala
370                 375                 380

Gln Pro Val Tyr Glu Thr Val Gln Arg Pro Leu Asp Arg Leu Phe Ser
385                 390                 395                 400

Ser Ile Val Thr Val Ala Glu Gln Lys Tyr Gln Ser Thr Leu Trp Asp
                405                 410                 415

Lys Ser Lys Lys Leu Ala Glu Gln Ala Ala Ile Val Cys Leu Arg
            420                 425                 430

Ser Gln Gly Leu Pro Glu Gly Arg Leu Gly Glu Ser Pro Ser Leu
            435                 440                 445

His Lys Arg Lys Arg Glu Ala Pro Asp Gln Asp Pro Gly Gly Pro Arg
450                 455                 460

Ala Gln Glu Leu Ala Gln Pro Gly Asp Leu Cys Lys Lys Pro Phe Val
465                 470                 475                 480

Ala Leu Gly Ser Gly Glu Glu Ser Pro Leu Glu Gly Trp
```

<210> SEQ ID NO 3
<211> LENGTH: 21
<212> TYPE: DNA
<213> ORGANISM: Artificial Sequence
<220> FEATURE:
<223> OTHER INFORMATION: An artificially synthesized primer sequence
      for RT-PCR

<400> SEQUENCE: 3
gaccacatcc aacagtattc g                                          21

<210> SEQ ID NO 4
<211> LENGTH: 21
<212> TYPE: DNA
<213> ORGANISM: Artificial Sequence
<220> FEATURE:
<223> OTHER INFORMATION: An artificially synthesized primer sequence
      for RT-PCR

<400> SEQUENCE: 4
tgccaggaca tctaacttct g                                          21

<210> SEQ ID NO 5
<211> LENGTH: 21
<212> TYPE: DNA
<213> ORGANISM: Artificial Sequence
<220> FEATURE:
<223> OTHER INFORMATION: An artificially synthesized primer sequence
      for RT-PCR

<400> SEQUENCE: 5
gaggtgatag cattgctttc g                                          21

<210> SEQ ID NO 6
<211> LENGTH: 21
<212> TYPE: DNA
<213> ORGANISM: Artificial Sequence
<220> FEATURE:
<223> OTHER INFORMATION: An artificially synthesized primer sequence
      for RT-PCR

<400> SEQUENCE: 6
caagtcagtg tacaggtaag c                                          21

<210> SEQ ID NO 7
<211> LENGTH: 19
<212> TYPE: DNA
<213> ORGANISM: Artificial Sequence
<220> FEATURE:
<223> OTHER INFORMATION: An artificially synthesized target sequence
      for siRNA

<400> SEQUENCE: 7
gaagcagcac gacttcttc                                             19

<210> SEQ ID NO 8
<211> LENGTH: 19
<212> TYPE: DNA
<213> ORGANISM: Artificial Sequence
<220> FEATURE:
<223> OTHER INFORMATION: An artificially synthesized target sequence
      for siRNA

<400> SEQUENCE: 8
cgtacgcgga atacttcga                                             19

<210> SEQ ID NO 9
<211> LENGTH: 19
<212> TYPE: DNA
<213> ORGANISM: Artificial Sequence
<220> FEATURE:
<223> OTHER INFORMATION: An artificially synthesized target sequence
      for siRNA

<400> SEQUENCE: 9
gcgcgctttg taggattcg                                                 19

<210> SEQ ID NO 10
<211> LENGTH: 19
<212> TYPE: DNA
<213> ORGANISM: Artificial Sequence
<220> FEATURE:
<223> OTHER INFORMATION: An artificially synthesized target sequence
      for siRNA

<400> SEQUENCE: 10
tgaggtgctc agcacagtg                                                 19

<210> SEQ ID NO 11
<211> LENGTH: 19
<212> TYPE: DNA
<213> ORGANISM: Artificial Sequence
<220> FEATURE:
<223> OTHER INFORMATION: An artificially synthesized target sequence
      for siRNA

<400> SEQUENCE: 11
gttggcacag cctgtgtat                                                 19

<210> SEQ ID NO 12
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 12
tcccgaagca gcacgacttc ttcttcaaga gagaagaagt cgtgctgctt c             51

<210> SEQ ID NO 13
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 13
aaaagaagca gcacgacttc ttctctcttg aagaagaagt cgtgctgctt c             51

<210> SEQ ID NO 14
<211> LENGTH: 47
<212> TYPE: DNA
<213> ORGANISM: Artificial Sequence
<220> FEATURE:
<223> OTHER INFORMATION: An artificially synthesized hairpin sequence
      for siRNA

<400> SEQUENCE: 14
gaagcagcac gacttcttct tcaagagaga agaagtcgtg ctgcttc                  47

```
<210> SEQ ID NO 15
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 15
tccccgtacg cggaatactt cgattcaaga gatcgaagta ttccgcgtac g            51

<210> SEQ ID NO 16
<211> LENGTH: 52
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 16
aaaacgtacg cggaatactt cgatctcttg aaatcgaagt attccgcgta cg           52

<210> SEQ ID NO 17
<211> LENGTH: 47
<212> TYPE: DNA
<213> ORGANISM: Artificial Sequence
<220> FEATURE:
<223> OTHER INFORMATION: An artificially synthesized hairpin sequence
      for siRNA

<400> SEQUENCE: 17
cgtacgcgga atacttcgat tcaagagatc gaagtattcc gcgtacg                 47

<210> SEQ ID NO 18
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 18
tcccgcgcgc tttgtaggat tcgttcaaga gacgaatcct acaaagcgcg c            51

<210> SEQ ID NO 19
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 19
aaaagcgcgc tttgtaggat tcgtctcttg aacgaatcct acaaagcgcg c            51

<210> SEQ ID NO 20
<211> LENGTH: 47
<212> TYPE: DNA
<213> ORGANISM: Artificial Sequence
<220> FEATURE:
<223> OTHER INFORMATION: An artificially synthesized hairpin sequence
      for siRNA

<400> SEQUENCE: 20
gcgcgctttg taggattcgt tcaagagacg aatcctacaa agcgcgc                 47
```

<210> SEQ ID NO 21
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 21
tccctgaggt gctcagcaca gtgttcaaga gacactgtgc tgagcacctc a            51

<210> SEQ ID NO 22
<211> LENGTH: 51
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 22
aaaatgaggt gctcagcaca gtgtctcttg aacactgtgc tgagcacctc a            51

<210> SEQ ID NO 23
<211> LENGTH: 47
<212> TYPE: DNA
<213> ORGANISM: Artificial Sequence
<220> FEATURE:
<223> OTHER INFORMATION: An artificially synthesized hairpin sequence
      for siRNA

<400> SEQUENCE: 23
tgaggtgctc agcacagtgt tcaagagaca ctgtgctgag cacctca                 47

<210> SEQ ID NO 24
<211> LENGTH: 50
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 24
tcccgttggc acagcctgtg tattcaagag aatacacagg ctgtgccaac              50

<210> SEQ ID NO 25
<211> LENGTH: 50
<212> TYPE: DNA
<213> ORGANISM: Artificial Sequence
<220> FEATURE:
<223> OTHER INFORMATION: An artificially synthesized oligonucleotide
      sequence for siRNA

<400> SEQUENCE: 25
aaaagttggc acagcctgtg tatctcttga atacacagg ctgtgccaac               50

<210> SEQ ID NO 26
<211> LENGTH: 46
<212> TYPE: DNA
<213> ORGANISM: Artificial Sequence
<220> FEATURE:
<223> OTHER INFORMATION: An artificially synthesized hairpin sequence
      for siRNA

<400> SEQUENCE: 26
gttggcacag cctgtgtatt caagagaata caggctgt gccaac                    46

<210> SEQ ID NO 27

<211> LENGTH: 493
<212> TYPE: PRT
<213> ORGANISM: Mus musculus

<400> SEQUENCE: 27

```
Met Ile Val Asn Ser Leu Ser Leu Cys Tyr His Asn Lys Leu Ile Leu
 1               5                  10                  15

Ala Pro Met Val Arg Val Gly Thr Leu Pro Met Arg Leu Leu Ala Leu
            20                  25                  30

Asp Tyr Gly Ala Asp Ile Val Tyr Cys Glu Glu Leu Ile Asp Leu Lys
        35                  40                  45

Met Leu Gln Cys Lys Arg Val Val Asn Glu Val Leu Ser Thr Val Asp
50                  55                  60

Phe Val Ala Pro Asp Asp Arg Val Val Phe Arg Thr Cys Glu Arg Glu
65                  70                  75                  80

Gln Ser Arg Val Val Phe Gln Met Gly Thr Ser Asp Ala Glu Arg Ala
                85                  90                  95

Leu Ala Val Ala Arg Leu Val Glu Asn Asp Val Ala Gly Ile Asp Val
            100                 105                 110

Asn Met Gly Cys Pro Lys Glu Tyr Ser Thr Lys Gly Met Gly Ala
        115                 120                 125

Ala Leu Leu Ser Asp Pro Asp Lys Ile Glu Lys Ile Leu Ser Thr Leu
    130                 135                 140

Val Lys Gly Thr His Arg Pro Val Thr Cys Lys Ile Arg Ile Leu Pro
145                 150                 155                 160

Ser Leu Glu Asp Thr Leu Asn Leu Val Lys Arg Ile Glu Arg Thr Gly
                165                 170                 175

Ile Ser Ala Ile Ala Val His Gly Arg Asn Arg Asp Glu Arg Pro Gln
            180                 185                 190

His Pro Val Ser Cys Glu Val Ile Arg Ala Ile Ala Glu Thr Leu Ser
        195                 200                 205

Ile Pro Val Ile Ala Asn Gly Gly Ser His Asp His Ile Gln Gln His
    210                 215                 220

Val Asp Ile Glu Asp Phe Arg Gln Ala Thr Ala Ala Ser Ser Val Met
225                 230                 235                 240

Val Ala Arg Ala Ala Met Trp Asn Pro Ser Ile Phe Leu Lys Asp Gly
                245                 250                 255

Leu Arg Pro Leu Glu Glu Val Met Gln Lys Tyr Ile Arg Tyr Ala Val
            260                 265                 270

Gln Tyr Asp Asn His Tyr Thr Asn Thr Lys Tyr Cys Leu Cys Gln Met
        275                 280                 285

Leu Arg Glu Gln Leu Glu Ser Pro Gln Gly Arg Leu Leu His Ala Ala
    290                 295                 300

Gln Ser Ser Gln Glu Ile Cys Glu Ala Phe Gly Leu Gly Ala Phe Tyr
305                 310                 315                 320

Glu Glu Thr Ile Arg Glu Leu Asp Ala Arg Ala Asp Leu Leu Ala
                325                 330                 335

Lys Thr Pro Glu Ala Val Glu Glu Pro Ala Glu Asp Thr Ser Gly Ile
            340                 345                 350

Ile Lys Met Ala Ile Arg Phe Asp Arg Arg Ala Tyr Pro Pro Gln Ile
        355                 360                 365

Thr Pro Lys Met Cys Leu Leu Glu Trp Cys Arg Arg Glu Lys Leu Pro
    370                 375                 380

Gln Pro Val Tyr Glu Thr Val Gln Arg Thr Ile Asp Arg Met Phe Cys
```

-continued

```
               385                 390                 395                 400
Ser Val Val Thr Val Ala Glu Gln Lys Tyr Gln Ser Thr Leu Trp Asp
                    405                 410                 415
Lys Ser Lys Lys Leu Ala Glu Gln Thr Ala Ile Val Cys Leu Arg
                    420                 425                 430
Ser Gln Gly Leu Pro Glu Gly Arg Leu Gly Glu Ser Pro Ser Leu
                    435                 440                 445
Asn Lys Arg Lys Arg Glu Ala Pro Asp Gln Asp Pro Gly Pro Arg
            450                 455                 460
Val Gln Glu Pro Ala Leu Pro Gly Glu Ile Cys Lys Lys Pro Phe Val
465                 470                 475                 480
Thr Leu Asp Ser Ser Glu Glu Asn Leu Leu Glu Gly Cys
                    485                 490

<210> SEQ ID NO 28
<211> LENGTH: 531
<212> TYPE: PRT
<213> ORGANISM: Rattus norvegicus

<400> SEQUENCE: 28

Met Ile Val Asn Ser Leu Ser Leu Cys Tyr His Asn Lys Leu Ile Leu
 1               5                  10                  15
Ala Pro Met Val Arg Val Gly Thr Leu Pro Met Arg Leu Leu Ala Leu
                20                  25                  30
Asp Tyr Gly Ala Asp Ile Val Tyr Cys Glu Glu Leu Ile Asp Leu Lys
            35                  40                  45
Met Leu Gln Cys Arg Arg Val Val Asn Glu Val Leu Ser Thr Val Asp
        50                  55                  60
Phe Val Ala Pro Asp Asp Arg Val Val Phe Arg Thr Cys Glu Arg Glu
65                  70                  75                  80
Gln Ser Arg Val Val Phe Gln Met Gly Thr Ser Asp Ala Glu Arg Ala
                85                  90                  95
Leu Ala Val Ala Arg Leu Val Glu Asn Asp Val Ala Gly Ile Asp Val
                100                 105                 110
Asn Met Gly Cys Pro Lys Glu Tyr Ser Thr Lys Gly Gly Met Gly Ala
            115                 120                 125
Ala Leu Leu Ser Asp Pro Asp Lys Ile Glu Lys Ile Leu Ser Thr Leu
        130                 135                 140
Val Lys Gly Thr His Arg Pro Val Thr Cys Lys Ile Arg Ile Leu Pro
145                 150                 155                 160
Ser Leu Glu Asp Thr Leu Asn Leu Val Lys Arg Ile Glu Arg Thr Gly
                165                 170                 175
Ile Ser Ala Ile Ala Val His Gly Arg Asn Arg Asp Glu Arg Pro Gln
            180                 185                 190
His Pro Val Ser Cys Glu Val Ile Arg Ala Ile Ala Glu Thr Leu Ser
        195                 200                 205
Ile Pro Val Ile Ala Lys Val Leu Ile Val Glu Gly Leu Leu Lys Leu
    210                 215                 220
Thr Asp Asn Glu Arg Gln Arg Ser Ser Gly Asn Thr Gly Arg Phe His
225                 230                 235                 240
Tyr Gly Ile Leu Pro Asn Pro Leu Leu Leu Phe Ser Gly Gly Ser His
                245                 250                 255
Asp His Ile Gln Gln His Leu Asp Ile Glu Asp Phe Arg Gln Ala Thr
            260                 265                 270
```

```
Ala Ala Ser Ser Val Met Val Ala Arg Ala Ala Met Trp Asn Pro Ser
        275                 280                 285

Ile Phe Leu Lys Asp Gly Leu Arg Pro Leu Glu Glu Val Met Gln Lys
290                 295                 300

Tyr Ile Arg Tyr Ala Val Gln Tyr Asp Asn His Tyr Thr Asn Thr Lys
305                 310                 315                 320

Tyr Cys Leu Cys Gln Met Leu Arg Glu Gln Leu Glu Ser Pro Gln Gly
                325                 330                 335

Arg Met Leu His Ala Ala Gln Ser Ser Gln Glu Ile Cys Glu Ala Phe
            340                 345                 350

Gly Leu Gly Thr Phe Tyr Glu Asp Thr Ile Arg Glu Leu Asp Ala Arg
        355                 360                 365

Arg Ala Asp Leu Leu Ala Lys Thr Pro Glu Ala Val Glu Glu Pro Ala
    370                 375                 380

Glu Asp Thr Ser Gly Ile Ile Lys Met Ala Ile Arg Phe Asp Arg Arg
385                 390                 395                 400

Ala Tyr Pro Pro Gln Ile Thr Pro Lys Thr Cys Leu Leu Glu Trp Cys
                405                 410                 415

Arg Arg Glu Lys Leu Pro Gln Pro Val Tyr Glu Thr Val Gln Arg Pro
            420                 425                 430

Ile Asp Arg Met Phe Cys Ser Val Val Thr Val Ala Glu Gln Lys Tyr
        435                 440                 445

Gln Ser Thr Leu Trp Asp Lys Ser Lys Lys Leu Ala Glu Gln Thr Ala
    450                 455                 460

Ala Ile Val Cys Leu Arg Ser Gln Gly Leu Pro Glu Gly Arg Leu Gly
465                 470                 475                 480

Glu Glu Asn Pro Ser Leu Asn Lys Arg Lys Arg Glu Ala Pro Asn Gln
                485                 490                 495

Asp Pro Gly Gly Pro Arg Val Gln Glu Thr Ala Leu Pro Gly Glu Ile
            500                 505                 510

Cys Lys Lys Pro Phe Val Thr Leu Glu Ser Ser Glu Glu Asn Leu Leu
        515                 520                 525

Glu Gly Cys
530

<210> SEQ ID NO 29
<211> LENGTH: 473
<212> TYPE: PRT
<213> ORGANISM: Drosophila melanogaster

<400> SEQUENCE: 29

Met Leu Arg Leu Pro Thr Ile Leu Arg Lys Ser Phe Ser Met Lys Thr
1               5                   10                  15

Arg Gln Arg Leu Asp Tyr Arg Asn Lys Leu Ile Leu Ala Pro Met Val
            20                  25                  30

Arg Val Gly Thr Leu Pro Met Arg Leu Leu Ala Leu Glu Met Gly Ala
        35                  40                  45

Asp Ile Val Tyr Thr Glu Glu Leu Val Asp Ile Lys Leu Ile Lys Ser
    50                  55                  60

Ile Arg Arg Pro Asn Pro Ala Leu Gly Thr Val Asp Phe Val Asp Pro
65                  70                  75                  80

Ser Asp Gly Thr Ile Val Phe Arg Thr Cys Ala Gln Glu Thr Ser Arg
                85                  90                  95

Leu Val Leu Gln Met Gly Thr Ser Asp Ala Gly Arg Ala Leu Ala Val
            100                 105                 110
```

Gly Lys Leu Leu Gln Arg Asp Ile Ser Gly Leu Asp Ile Asn Met Gly
            115                 120                 125

Cys Pro Lys Glu Phe Ser Thr Lys Gly Gly Met Gly Ala Ala Leu Leu
        130                 135                 140

Ala Asp Pro Asp Lys Ala Ala His Ile Leu Arg Thr Leu Cys Ser Gly
145                 150                 155                 160

Leu Asp Ile Pro Val Thr Cys Lys Ile Arg Ile Leu Pro Asp Val Glu
                165                 170                 175

Gly Thr Ile Asp Leu Val Gln Lys Leu Ala Ala Thr Gly Ile Ala Ala
            180                 185                 190

Ile Gly Val His Ala Arg Thr Arg Asp Glu Arg Pro Gln His Pro Ala
        195                 200                 205

His Pro Glu Val Leu Arg Ala Val Ala Gln Ala Val Asp Ile Pro Ile
    210                 215                 220

Ile Ala Asn Gly Gly Ser Lys Asn Met His Cys Tyr Asp Asp Leu Arg
225                 230                 235                 240

Lys Phe Gln Met Glu Cys Gly Ala Asp Ser Val Met Val Ala Arg Ala
                245                 250                 255

Ala Gln Ile Asn Val Ser Ile Phe Arg Pro Glu Gly Leu Leu Pro Met
            260                 265                 270

Asp Glu Leu Ile Glu Lys Tyr Leu Arg Leu Cys Val Asp Tyr Asp Asn
        275                 280                 285

Ala Pro His Asn Ala Lys Tyr Cys Val Gln Ser Ile Leu Arg Glu Leu
    290                 295                 300

Gln Glu Thr Pro Arg Gly Lys Arg Phe Leu Gln Cys Gln Thr Leu Gln
305                 310                 315                 320

Gln Ile Cys Glu Ile Trp Glu Leu Gly Asp Tyr Cys Arg Arg Lys Gln
                325                 330                 335

Arg Glu Leu Lys Thr Met Gly Asn Ser Gly Arg Ala Glu Val Glu Pro
            340                 345                 350

Pro Glu Ala Leu Ala Lys Arg Gln Lys Leu Glu Asp Ala Ala Ile Ala
        355                 360                 365

Ile Thr Asp Glu Tyr Asp Gly Ile Ile Cys Arg His Met Pro Phe Leu
    370                 375                 380

Arg Ser Thr Tyr Pro Ser Asp Asn His Leu Pro Lys Thr Gln Leu Tyr
385                 390                 395                 400

Val His Ala Val Lys Thr Gly Lys Ser Pro Pro Ala Tyr Glu Thr Gln
                405                 410                 415

Gln Cys Asp Lys Leu Phe Arg Ser Ile Cys Thr Tyr Asp Gly Gln Arg
            420                 425                 430

Phe Ser Ser Ser Phe Trp Glu Lys Asn Lys Gln Ala Glu Gln Gly
        435                 440                 445

Ala Ala Leu Val Ala Leu Leu His Leu Gly Gln Leu Glu Ala Glu Val
    450                 455                 460

Leu Arg Asp Asn Gly Ser Leu Leu Asn
465                 470

<210> SEQ ID NO 30
<211> LENGTH: 436
<212> TYPE: PRT
<213> ORGANISM: Caenorhabditis elegans

<400> SEQUENCE: 30

Met Ser Asp Leu Tyr Arg Asn Lys Lys Ile Leu Ala Pro Met Val Arg

-continued

```
  1               5                   10                  15
Ala Gly Arg Thr Pro Leu Arg Leu Leu Cys Leu Lys Tyr Gly Ala Asp
                20                  25                  30

Leu Cys Tyr Thr Glu Glu Ile Val Asp Lys Lys Leu Ile Glu Ala Thr
                35                  40                  45

Arg Val Val Asn Glu Ala Leu Gly Thr Ile Asp Tyr Arg Asn Gly Asp
                50                  55                  60

Asp Ile Ile Leu Arg Leu Ala Pro Glu Glu Lys Gly Arg Cys Ile Leu
 65                 70                  75                  80

Gln Ile Gly Thr Asn Ser Gly Glu Lys Ala Lys Ile Ala Gln Ile
                85                  90                  95

Val Gly Asp Asp Val Ala Gly Ile Asp Val Asn Met Gly Cys Pro Lys
                100                 105                 110

Pro Phe Ser Ile His Cys Gly Met Gly Ala Ala Leu Leu Thr Gln Thr
                115                 120                 125

Glu Lys Ile Val Asp Ile Leu Thr Ser Leu Lys Ser Ala Ala Lys Val
                130                 135                 140

Pro Val Thr Cys Lys Ile Arg Val Leu Asp Asp Pro Glu Asp Thr Leu
145                 150                 155                 160

Lys Leu Val Gln Glu Ile Glu Lys Cys Arg Val Ser Ala Leu Gly Val
                165                 170                 175

His Gly Arg Arg Arg Asp Glu Arg Gln Pro Asp Lys Cys Arg Ile Asp
                180                 185                 190

Glu Ile Arg Asp Val Ala Gln Ala Val Gln Ser Ile Pro Val Ile Ser
                195                 200                 205

Asn Gly Leu Ser Asp Glu Ile Glu Gln Tyr Ser Asp Phe Glu Lys Tyr
                210                 215                 220

Gln Leu Leu Thr Glu Thr Ser Ser Thr Met Ile Ala Arg Lys Ala Leu
225                 230                 235                 240

Ser Thr Pro Ser Ile Phe Arg Arg Glu Gly Cys Leu Asp Lys Tyr Glu
                245                 250                 255

Asp Ile Arg Asn Phe Leu Glu Leu Ala Cys Gln Tyr Asp Glu Ser Tyr
                260                 265                 270

Thr Met Thr Lys Tyr Val Val Gln Arg Ile Leu Gly Ala Asp Gln Glu
                275                 280                 285

Tyr Asp Pro Arg Gly Lys Ala Thr Val Ala Ala Gly Ser Val Leu Gln
                290                 295                 300

Ile Cys Lys Ala Phe Gly Met Glu Asp Val Tyr Asp Lys Trp Arg Asp
305                 310                 315                 320

Glu Arg Lys Lys Lys Gln Ser Lys Lys Arg Ala Arg Val Asp Asp
                325                 330                 335

Gly Val Tyr Asn Ile Glu Val Ser Phe Pro Leu Lys Arg Leu Lys Asn
                340                 345                 350

Ser Val Gly Phe Ser Pro Thr Pro Lys Met Val Leu His Asp Tyr Cys
                355                 360                 365

Val Glu Thr Lys Ile Pro Lys Ala Thr Tyr Glu Val Val Lys Arg Asp
                370                 375                 380

Asp Lys Arg Phe Val Ala Thr Ala Cys Ile Gly Asp Lys Lys Tyr Arg
385                 390                 395                 400

Ser Gly Ile Gly Gln Pro Asn Leu Arg Met Ala Glu Gln Val Ala Ala
                405                 410                 415

Leu Ala Ala Leu His Gly Met Asn Ile Arg Asn Leu Leu Val Gly Asn
                420                 425                 430
```

Trp Glu Glu Glu
        435

<210> SEQ ID NO 31
<211> LENGTH: 384
<212> TYPE: PRT
<213> ORGANISM: Saccharomyces cerevisiae

<400> SEQUENCE: 31

Met Val Thr Tyr Ala Gly Lys Leu Val Leu Ala Pro Met Val Arg Ala
  1               5                  10                  15

Gly Glu Leu Pro Thr Arg Leu Met Ala Leu Ala His Gly Ala Asp Leu
             20                  25                  30

Val Trp Ser Pro Glu Ile Ile Asp Lys Lys Leu Ile Gln Cys Val Arg
         35                  40                  45

Lys Glu Asn Thr Ala Leu Gln Thr Val Asp Tyr Val Val Pro Ser Lys
     50                  55                  60

Val Gln Thr Arg Pro Glu Thr Leu Val Phe Arg Thr Tyr Pro Lys Leu
 65                  70                  75                  80

Glu Ser Ser Lys Leu Ile Phe Gln Ile Gly Ser Ala Ser Pro Ala Leu
                 85                  90                  95

Ala Thr Gln Ala Ala Leu Lys Val Ile Asn Asp Val Ser Gly Ile Asp
            100                 105                 110

Val Asn Met Gly Cys Pro Lys His Phe Ser Ile His Ser Gly Met Gly
        115                 120                 125

Ser Ala Leu Leu Arg Thr Pro Asp Thr Leu Cys Leu Ile Leu Lys Glu
    130                 135                 140

Leu Val Lys Asn Val Gly Asn Pro His Ser Lys Pro Ile Ser Val Lys
145                 150                 155                 160

Ile Arg Leu Leu Asp Thr Lys Gln Asp Thr Leu Gln Leu Val Lys Arg
                165                 170                 175

Leu Cys Ala Thr Gly Ile Thr Asn Leu Thr Val His Cys Arg Lys Thr
            180                 185                 190

Glu Met Arg Asn Arg Glu Gln Pro Ile Thr Asp Tyr Ile Ala Glu Ile
        195                 200                 205

Tyr Glu Ile Cys Gln Ala Asn Asn Val Ser Leu Ile Val Asn Gly Ala
    210                 215                 220

Ile Arg Asp Arg Ser His Phe His Asp Leu Gln Ala Asn His Trp Lys
225                 230                 235                 240

Asn Thr Asn Ile Gly Gly Met Ile Ala Glu Cys Ala Glu Arg Asp Pro
                245                 250                 255

Thr Val Phe Asp His Thr Ser Lys Pro Ser Glu Asp Gly Pro Ser Trp
            260                 265                 270

Val Val Ala Cys Arg Glu Phe Ile Gln Trp Ala Thr Lys Phe Asp Asn
        275                 280                 285

His Ile Gly Asn Thr Lys Tyr Met Leu Ser Arg Ile Val Pro Gly Lys
    290                 295                 300

Ser Val Phe Phe Gln Tyr Phe Ala Arg Cys Lys Ser Pro Glu Glu Val
305                 310                 315                 320

Ser Phe Val Leu Lys Gln Leu Asn Asp Asp Gly Ser Ala Gln Thr Asp
                325                 330                 335

Pro Ser Glu Tyr Leu Glu Asn Cys Arg Ala Gln Glu Lys Ala Leu Lys
            340                 345                 350

Asn Ala Asn Ala Ile Ala Lys Gln Lys Arg Lys Gln Thr Asp His Ile

```
                355                 360                 365
Gly Ser Asp Thr Lys Lys Gln Lys Val Val Pro Leu Pro Thr Asp Ile
    370                 375                 380
```

<210> SEQ ID NO 32
<211> LENGTH: 423
<212> TYPE: PRT
<213> ORGANISM: Saccharomyces cerevisiae

<400> SEQUENCE: 32

```
Met Thr Glu Pro Ala Leu Ser Ser Ala Asn Asn Ala Leu Met Gln Lys
  1               5                  10                  15

Leu Thr Gly Arg Gln Leu Phe Asp Lys Ile Gly Arg Pro Thr Arg Ile
             20                  25                  30

Val Ala Pro Met Val Asp Gln Ser Glu Leu Ala Trp Arg Ile Leu Ser
         35                  40                  45

Arg Arg Tyr Gly Ala Thr Leu Ala Tyr Thr Pro Met Leu His Ala Lys
     50                  55                  60

Leu Phe Ala Thr Ser Lys Lys Tyr Arg Glu Asp Asn Trp Ser Ser Leu
 65                  70                  75                  80

Asp Gly Ser Ser Val Asp Arg Pro Leu Val Val Gln Phe Cys Ala Asn
                 85                  90                  95

Asp Pro Glu Tyr Leu Leu Ala Ala Lys Leu Val Glu Asp Lys Cys
            100                 105                 110

Asp Ala Val Asp Leu Asn Leu Gly Cys Pro Gln Gly Ile Ala Lys Lys
        115                 120                 125

Gly His Tyr Gly Ser Phe Leu Met Glu Glu Trp Asp Leu Ile His Asn
    130                 135                 140

Leu Ile Asn Thr Leu His Lys Asn Leu Lys Val Pro Val Thr Ala Lys
145                 150                 155                 160

Ile Arg Ile Phe Asp Asp Cys Glu Lys Ser Leu Asn Tyr Ala Lys Met
                165                 170                 175

Val Leu Asp Ala Gly Ala Gln Phe Leu Thr Val His Gly Arg Val Arg
            180                 185                 190

Glu Gln Lys Gly Gln Lys Thr Gly Leu Ala Asn Trp Glu Thr Ile Lys
        195                 200                 205

Tyr Leu Arg Asp Asn Leu Pro Lys Glu Thr Val Phe Phe Ala Asn Gly
    210                 215                 220

Asn Ile Leu Tyr Pro Glu Asp Ile Ser Arg Cys Met Glu His Ile Gly
225                 230                 235                 240

Ala Asp Ala Val Met Ser Ala Glu Gly Asn Leu Tyr Asn Pro Gly Val
                245                 250                 255

Phe Asn Val Gly Gln Thr Lys Asn Lys Glu Lys Ile Phe Pro Arg Val
            260                 265                 270

Asp Lys Ile Ile Arg Glu Tyr Phe Gln Ile Val Lys Glu Cys Gln Glu
        275                 280                 285

Ser Lys Ala Ser Lys Thr Ala Met Lys Ser His Phe Phe Lys Ile Leu
    290                 295                 300

Arg Pro Phe Leu Pro His His Thr Asp Ile Arg Ser Thr Leu Ala Thr
305                 310                 315                 320

Met Asn Ala Lys Ala Thr Trp Glu Glu Trp Glu Glu Gln Val Val Lys
                325                 330                 335

Pro Val Glu Lys Val Val Gln Glu Ile Phe Glu Gln Pro Asp Ile Ala
            340                 345                 350
```

```
Ile Lys Asp Glu Ile Thr Ile Gly Glu Lys Gln Ser Trp Gly Gly Ser
        355                 360                 365
Tyr Arg Thr Val Pro Tyr Trp Arg Cys Gln Pro Tyr Phe Arg Pro Val
        370                 375                 380
Asn Gly Ile Thr Gly Asp Lys Arg Val Met Gln Gly Leu Ile Asp Glu
385                 390                 395                 400
Ser Val Asn Lys Lys Arg Lys Ala Asp Val Pro Leu Glu Ser Ala Asp
                405                 410                 415
Lys Lys Lys Asp Val Lys Ala
            420

<210> SEQ ID NO 33
<211> LENGTH: 10
<212> TYPE: PRT
<213> ORGANISM: Artificial Sequence
<220> FEATURE:
<223> OTHER INFORMATION: c-Myc-His epitope tag
<220> FEATURE:
<221> NAME/KEY: MOD_RES
<222> LOCATION: (10)...(10)
<223> OTHER INFORMATION: terminal Glu modified with 6 histidines

<400> SEQUENCE: 33

Leu Asp Glu Glu Ser Ile Leu Lys Gln Glu
1               5                   10
```

METHOD FOR DIAGNOSING NON-SMALL CELL LUNG CANCERS BY TRNA-DIHYDROURIDINE SYNTHASE ACTIVITY OF URLC8

PRIORITY

This application claims the benefit of U.S. Provisional Application Ser. No. 60/612,937, filed on Sep. 24, 2004, the contents of which are incorporated by reference herein in its entirety.

FIELD OF THE INVENTION

The present invention relates to lung cancer, more particularly non-small cell lung cancer, and the diagnosis and treatment thereof.

BACKGROUND OF THE INVENTION

Lung cancer is one of the most common causes of cancer death worldwide, and non-small cell lung cancer (NSCLC) accounts for nearly 80% of those cases (Greenlee, R. T., et al., (2001) CA Cancer J Clin, 51: 15-36.). Many genetic alterations associated with the development and progression of lung cancer have been reported, but the precise molecular mechanisms remain unclear (Sozzi, G. Eur J Cancer, (2001) 37 Suppl 7: S63-73.). Over the last decade, newly developed cytotoxic agents, including paclitaxel, docetaxel, gemcitabine, and vinorelbine, have emerged to offer multiple therapeutic choices for patients with advanced NSCLC; however, each of the new regimens can provide only modest survival benefits as compared to cisplatin-based therapies (Schiller, J. H. et al. (2002) N Engl J Med, 346: 92-98.; Kelly, K., et al. (2001) J Clin Oncol, 19: 3210-3218.). Hence, the development of new therapeutic strategies, such as molecular-targeted agents and antibodies, and cancer vaccines, are eagerly awaited.

Systematic analysis of expression levels of thousands of genes on cDNA microarrays is an effective approach to identifying unknown molecules involved in pathways of carcinogenesis, and can reveal candidate targets for development of novel therapeutics and diagnostics. The present inventors have been attempting to isolate novel molecular targets for diagnosis, treatment and prevention of NSCLC by analyzing genome-wide expression profiles of NSCLC cells on a cDNA microarray containing 23,040 genes, using pure populations of tumor cells prepared from 37 cancer tissues by laser-capture microdissection (Kikuchi, T. et al., Oncogene, (2003) 22: 2192-2205.; Zembutsu, H. et al. (2003) Int J Oncol, 23: 29-39.; Kakiuchi, S. et al. Mol Cancer Res, (2003) 1: 485-499.; Suzuki, C. et al., (2003) Cancer Res, 63: 7038-7041.). Through this genome wide cDNA microarray analysis, 642 up-regulated genes and 806 down-regulated genes have been identified as diagnostic markers and therapeutic targets for NSCLC (WO 2004/31413).

SUMMARY OF THE INVENTION

To verify the biological and clinicopathological significance of the respective gene products, tumor-tissue microarray analysis of clinical lung-cancer materials have been performed. This systematic approach revealed that a novel gene, tentatively named IMS-E21 (also known as URLC8: up-regulated in lung cancer 8, Accession No. AB101210; formerly FLJ20399), was frequently over-expressed in primary NSCLCs.

The URLC8 gene encodes a double-strand RNA binding motif (DSRM) domain. The lowered expression of this gene in normal tissues, elevated expression in NSCLCs, and reduced growth, proliferation and/or survival of transfected cells by the suppression of this gene together suggest that this gene might be useful as a novel diagnostic marker and target for new drugs and immunotherapy (WO2004/31413).

The URLC8 gene has been assigned to chromosome 16q22.2 and encodes a protein of 493 amino acids with 30% homology to S. cerevisiae Dus1 (dihydrouridine synthase 1), a member of UPF0034 (unclassified protein family 0034), which catalyses the reduction of the 5,6-double bond of a uridine residue on D-loop in tRNA (Xing, F. et al., RNA, (2002) 8: 370-381.), and contains conserved DSRM (double-strand RNA binding motif).

5,6-Dihydrouridine is a modified base found abundantly in the D-loops of tRNA from Archaea, Bacteria, and Eukarya. 5,6-Dihydrouridine is thought to be formed post-transcriptionally by the reduction of uridines in tRNA transcripts. The role of dihydrouridine in tRNA was presumed to increase the conformational flexibility of the tRNA. Interestingly, an increase in the level of dihydrouridine was previously reported in tumor-specific tRNA$^{Phe}$ purified from human malignant tissues (Kuchino, Y. and Borek, E. (1978) Nature, 271: 126-129.), however, its precise mechanism and biological contribution to tumorigenesis remain unclear (Dalluge, J. J. et al., (1996) Nucleic Acids Res, 24: 1073-1079.).

Herein the present inventors report the identification and functional characterization of a novel human tRNA-dihydrouridine synthase (DUS) protein, URLC8, in human lung tumors. The results herein suggest that overexpression of URLC8 plays a significant role in development/progression of lung cancer and that this molecule represents a potential target for development of novel therapeutic drugs.

The present invention is based in part on the discovery of the t-RNA dihydrouridine-synthase activity of URLC8, a polypeptide which is involved in the proliferation of lung cancer cells.

Accordingly, the present invention provides a method of diagnosing non-small cell lung cancer or a predisposition to developing non-small cell lung cancer in a subject, comprising determining a level of t-RNA dihydrouridine-synthase activity and/or t-RNA dihydrouridine in a biological sample derived from the subject, wherein an increase in said level as compared to a normal control level indicates that said subject suffers from or is at risk of developing non-small cell lung cancer.

The present invention also provides methods of predicting a lung squamous-cell carcinoma (SCC) prognosis. In some embodiments, the method comprises the steps of:

a. detecting a URLC8 expression level in a specimen collected from a subject whose SCC prognosis is to be predicted, and
b. indicating a poor prognosis when an elevated level of URLC8 expression is detected.

In a further embodiment, the present invention features a method of measuring t-RNA dihydrouridine-synthase activity by incubating a polypeptide under conditions suitable for synthesis of t-RNA dihydrouridine and detecting the t-RNA dihydrouridine synthesis level. The polypeptide is a URLC8 polypeptide or functional equivalent thereof. For example, the polypeptide may comprise the amino acid sequence of SEQ ID NO: 2. Alternatively, the polypeptide may comprise an amino acid sequence of SEQ ID NO: 2 where one or more amino acids are substituted, deleted, or inserted, so long as the resulting polypeptide retains the biological activity of the polypeptide of SEQ ID NO: 2. Biological activities of the polypeptide of SEQ ID No: 2 include, for example, the promotion of cell proliferation and the synthesis of t-RNA dihydrouridine. Additionally, the polypeptide may comprise a 493-amino acid protein encoded by the open reading frame of SEQ. ID. NO. 1, or a polynucleotide that hybridizes under stringent conditions, e.g., low or high, to the nucleotide sequence of SEQ ID NO: 1, so long as the resulting polynucleotide encodes a protein that retains the biological activity of the polypeptide of SEQ ID NO: 2. Examples of suitable low stringency conditions include, for example, 42° C., 2×SSC, 0.1% SDS, or preferably 50° C., 2×SSC, 0.1% SDS. Preferably, a high stringency condition is used. An example of a suitable high stringency condition includes, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In the context of the present invention, t-RNA dihydrouridine-synthase activity is defined as the catalysis of the reduction of the 5,6-double bond of a uridine residue on tRNA (FIG. 1c.). Synthesis of t-RNA dihydrouridine may be detected by conventional methods, such as those using a radioactive tRNA substrate or derivatives thereof. The substrate may be any compound capable of reduction of the 5,6-double bond of a uridine residue. An exemplary substrate is a tRNA having D-loop such as a tRNA$^{Phe}$ or other tRNA. The co-factor, e.g., the hydrogen donor, may be any compound capable of donating a hydrogen atom. For example, the co-factor may be a reduced form of nicotinamide adenine dinucleotide (NADH) or nicotinarnide adenine dinucleotide phosphate (NADPH). Suitable conditions for synthesis include, for example, basic buffer conditions know in the art such as Tris-HCl.

The present invention further provides methods of identifying an agent that modulates (e.g., increases or decreases) t-RNA dihydrouridine-synthase activity by incubating a polypeptide under conditions suitable for synthesis of t-RNA dihydrouridine in the presence of a test agent and determining the t-RNA dihydrouridine synthesis level. A decrease in the level of synthesis as compared to a normal control synthesis level indicates that the test agent is an inhibitor of t-RNA dihydrouridine-synthase activity. Compounds that inhibit (e.g., decreases) t-RNA dihydrouridine-synthase activity are useful for treating, preventing or alleviating a symptom of lung cancer. For example, such compounds may inhibit the proliferation of lung cancer cells. Alternatively, an increase in the level or activity as compared to a normal control level indicates that the test agent is an enhancer of t-RNA dihydrouridine-synthase activity. Herein, the phrase normal control level refers to a level of t-RNA dihydrouridine synthesis detected in the absence of the test compound.

The present invention also encompasses compositions and methods for treating or preventing of lung cancer by contacting a lung cancer cell with a compound identified as described above. In a further embodiment, the present invention provides for the use of a compound identified as described above, for manufacturing a pharmaceutical composition suitable for treating or preventing lung cancer. For example, a method of treating lung cancer may involve the step of administering to a mammal, e.g. a human patient having been diagnosed with such a disease state, with a composition containing a pharmaceutically effective amount of a compound identified as described above and a pharmaceutical carrier.

The present invention also provides a kit for the detecting the t-RNA dihydrouridine-synthase activity of a compound with a t-RNA dihydrouridine-synthase polypeptide or living cell expressing the polypeptide and reagent for detecting a t-RNA dihydrouridine-synthase activity. The reagents are preferably packaged together in the form of a kit. The reagents may be packaged in separate containers and may include, for example, a t-RNA dihydrouridine-synthase polypeptide, reagent for detecting a t-RNA dihydrouridine-synthase activity, a control reagent (positive and/or negative), and/or a detectable label. Instructions (e.g., written, tape, VCR, CD-ROM, etc.) for carrying out the assay are preferably included in the kit. The assay format of the kit may comprise any t-RNA dihydrouridine-synthase assay known in the art.

In a further embodiment, the present method may include the step of administering to a subject a small interfering RNA (siRNA) composition. In the context of the present invention, the siRNA composition reduces the expression of URLC8 .

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

a, Schematic structure of IMS-E21 (URLC8) protein. A member of UPF0034 (unclassified protein family 0034), Dus domain at N-terminal end, and DSRM (double-strand RNA binding motif) at C-terminal end were conserved in its protein structure, showing 30% homology to S. cerevisiae Dihydrouridine synthase 1 (DUS1), which catalyses the reduction of the 5,6-double bond of a uridine residue on tRNA. b, Alignment of the predicted amino acid sequences of the IMS-E21 (URLC8) SEQ ID NOS: 2 and 27-32. Shading indicates homologues residues. c, The structure of dihydrouridine in tRNA. d, Two-dimensional representation of a generic tRNA with the D-loop nucleotides.

Figure 2:
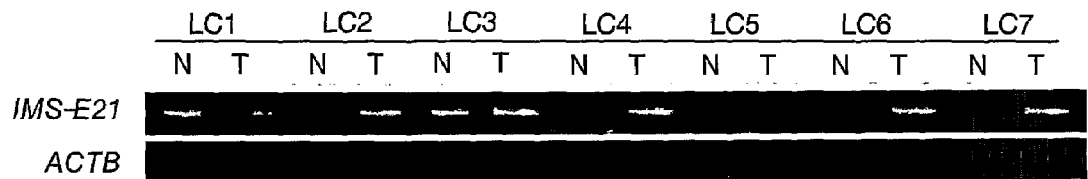
Figure 2:
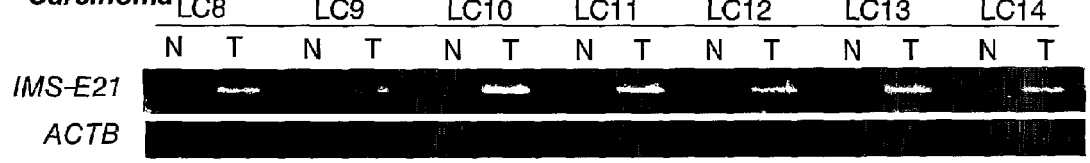
Figure 2:
Figure 2:
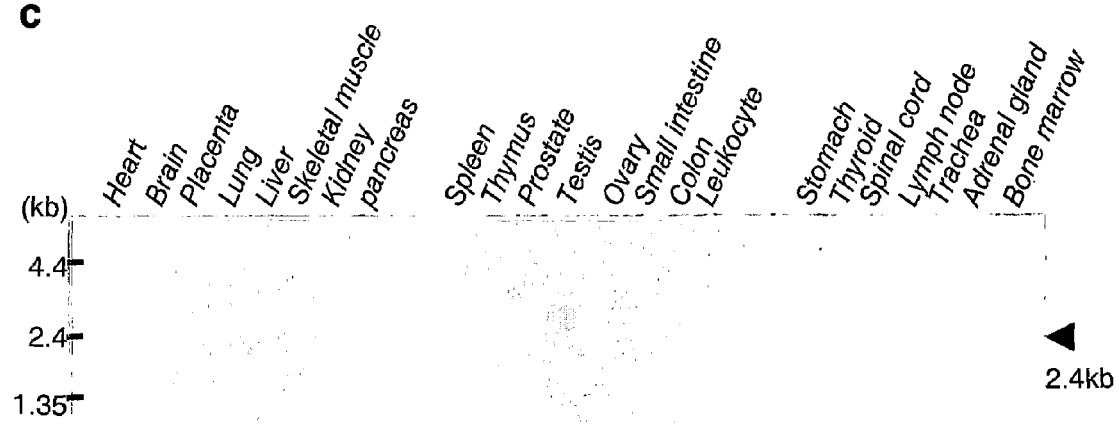

FIG. 2 depicts the expression of IMS-E21 (URLC8) in lung tumors and normal tissues.

a, Expression of IMS-E21 (URLC8) in clinical samples of NSCLC and corresponding normal lung tissues, examined by semi-quantitative RT-PCR. b, Expression of IMS-E21 (URLC8) in lung-cancer cell lines by semi-quantitative RT-PCR. c, Expression of IMS-E21 (URLC8) in human normal tissues, detected by multiple-tissue Northern-blot analysis.

Figure 3:
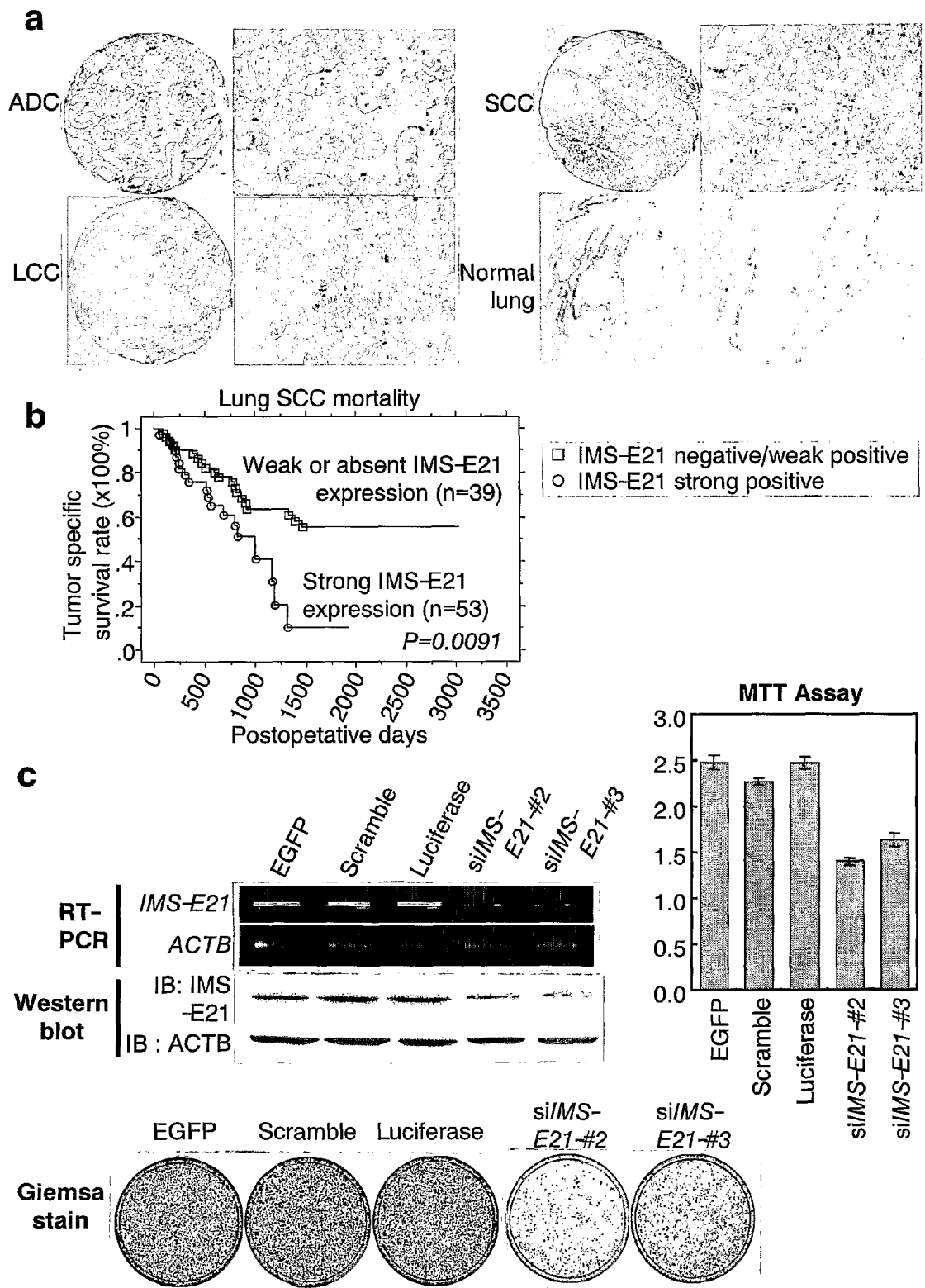

FIG. 3 depicts the results of the immunohistochemical study of IMS-E21 (URLC8) expression in NSCLC and inhibition of growth of NSCLC cells by siRNA against IMS-E21 (URLC8).

a, Immunohistochemical evaluation of representative samples from surgically-resected NSCLC tissues using anti-IMS-E21 (URLC8) polyclonal antibody on tissue microarrays. b, Kaplan-Meier analysis of tumor specific survival in lung SCC patients according to IMS-E21 (URLC8) expression. c, mRNA knock down effect in response to si-IMS-E21 (URLC8) or control siRNAs in LC319 cells, (left panels) analyzed by semi-quantitative RT-PCR (upper panels) and endogenous IMS-E21 (URLC8) protein knock down effect by western blotting (middle panels), and (lower panels) colony-formation assays. (right panels) MTT assays of LC319 cells transfected with specific siRNAs or control plasmids (EGFP, Scramble, or Luciferase).

Figure 4:
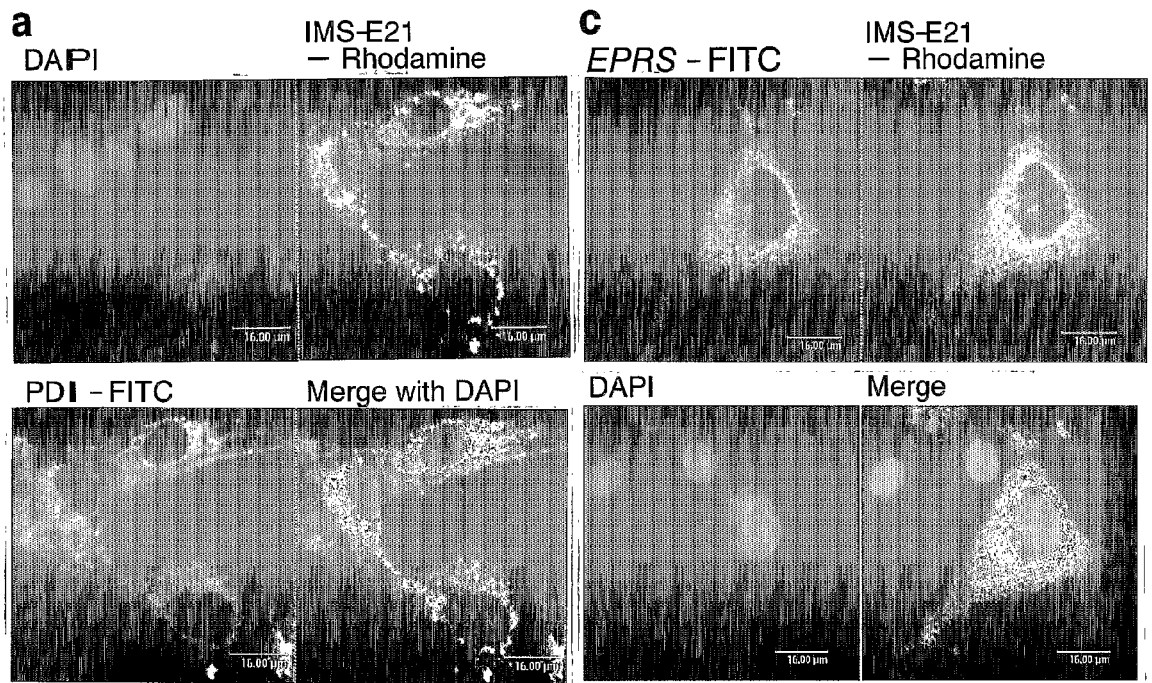
Figure 4:
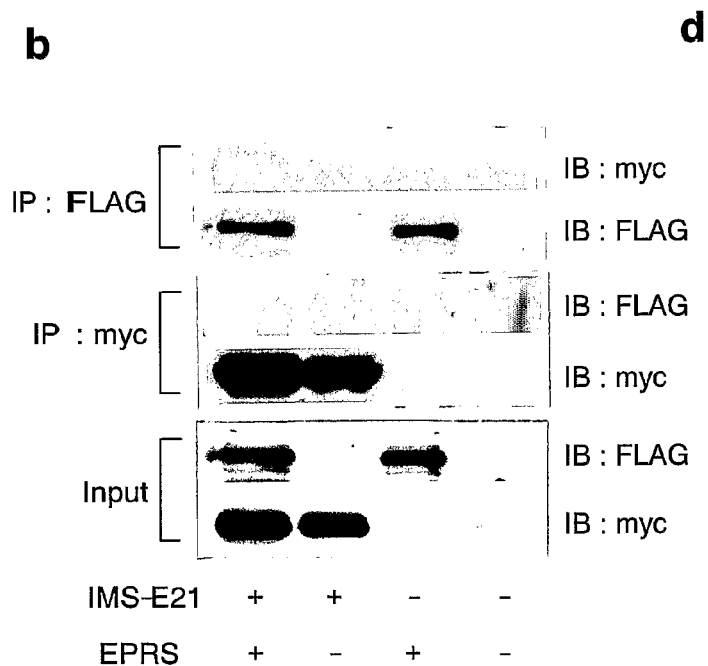
Figure 4:
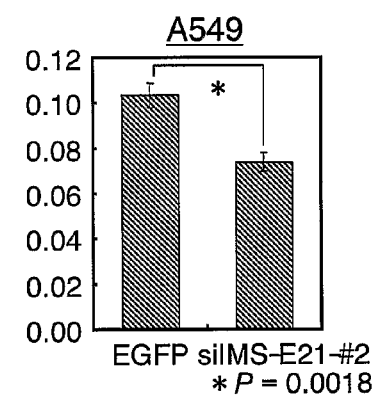
Figure 4:
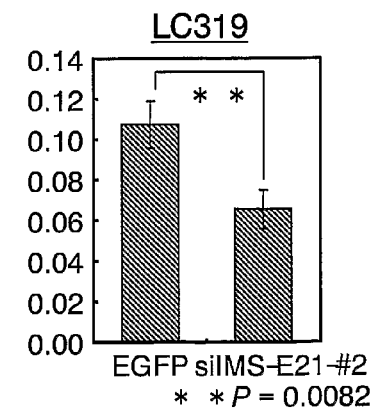

FIG. 4 depicts the characterization of IMS-E21 (URLC8) function in NSCLC cells. a, Subcellular localization of endogenous IMS-E21 (URLC8) in LC319 cells; staining is visible mainly in cytoplasm (Rhodamine). Co-localization of myc-tagged-IMS-E21 (URLC8) (Rhodamine) and endogenous PDI (Protein Disulfide Isomerase), which was an abundant protein of endoplasmic reticulum (ER) (FITC) was observed. b, Identification of EPRS as an IMS-E21 (URLC8) interacting protein. Reciprocal co-immunoprecipitation of IMS-E21 (URLC8) and EPRS, both of which had been transfected into LC319 cell extracts. Western-blot analysis of the cell extracts inmunuoprecipitated with anti-FLAG M2 monoclonal antibodies, detected myc-tagged-IMS-E21 (URLC8) protein in the immunoprecipitate. Western-blot of extracts immunoprecipitated with anti-myc antibodies, detected FLAG-tagged EPRS protein in the immunoprecipitate. c, Co-localization of myc-tagged-IMS-E21 (URLC8) and FLAG-tagged EPRS in LC319 cells. d, Reduction of tRNA dihydrouridine content in A549 and LC319 cells treated with siRNAs against IMS-E21 (URLC8).

DETAILED DESCRIPTION OF THE INVENTION

Overview:

Although advances have been made in development of molecular-targeting drugs for cancer therapy, the ranges of tumor types that respond as well as the effectiveness of the treatments are still very limited (Ranson, M., et al. (2002) J Clin Oncol, 20: 2240-2250.; Blackledge, G. and Averbuch, S. (2004) Br J Cancer, 90: 566-572.). Hence, it is urgent to develop new anti-cancer agents highly specific to malignant cells with minimal or no adverse reactions. A powerful strategy toward these ends would combine screening of up-regulated genes in cancer cells on the basis of genetic information obtained on cDNA microarrays with high-throughput screening of their effect on cell growth, by inducing loss-of-function phenotypes with RNAi systems, and with validation of the potential drug targets by analyzing hundreds of clinical samples on tissue microarray (Sauter, G., et al. (2003) Nat Rev Drug Discov, 2: 962-972.; Kononen, J., et al. (1998) Nat Med, 4: 844-847.). By pursuing such a strategy, the present inventors have demonstrated herein that IMS-E21 (URLC8) is not only frequently co-over-expressed in clinical NSCLC samples and cell lines, but also that the high levels of expression of the gene products are indispensable for the disease progression as well as growth of NSCLC cells.

IMS-E21 (URLC8) is assigned to chromosome 16q22.2 and encodes a protein of 493 amino acids with 30% homology to S. cerevisiae Dihydrouridine synthase 1 (DUS 1), a member of UPF0034 (unclassified protein family 0034), which catalyses the reduction of the 5,6-double bond of a uridine residue on tRNA (Xing, F., et al. (2002) RNA, 8: 370-381.), and with conserved double-strand RNA binding motif, DSRM. Several studies have revealed that tRNA modification enhances structural stabilization (Bjork, G. R., et al., (1987) Annu Rev Biochem, 56: 263-287.). In contrast, much less attention has been paid to modifications that potentially decrease regional stability and promote conformational flexibility of individual nucleotide residues. Dihydrouridine is the single most common form of post-translational modification in tRNA from bacteria and eukaryotes (Sprinzl, M., et al., (1998) Nucleic Acids Res, 26: 148-153.). The widespread presence of 5,6-dihydrouridine in the D-loop of tRNA has been known for decades, and some DUS enzymes have been identified in S. cerevisiae and E. coli, but the DUS enzyme with double-strand RNA binding motif in mammalian cells has not been previously identified (Xing, F., et al., (2002) RNA, 8: 370-381.; Kuchino, Y. and Borek, E. (1978) Nature, 271: 126-129.).

With regards to dihydrouridine in tRNA in tumor cells, interestingly, an increase in the level of dihydrouridine was previously reported in tumor-specific tRNA$^{Phe}$ purified from human malignant tissues. The role of dihydrouridine in tRNA may increase conformational flexibility of the tRNA, but its precise function remains unclear. To elucidate the biological function of IMS-E21 (URLC8) and its contribution to lung carcinogenesis, the sub-cellular localization of IMS-E21 (URLC8) protein in LC319cells was examined and found to be localized in ER. To clarify whether native IMS-E21 (URLC8) protein is required for tRNA-DUS activity in human NSCLC cells, IMS-E21 (URLC8)-siRNA vectors were transfected to A549 and LC319cell lines in which the IMS-E21 (URLC8) gene is highly expressed. In those lung-cancer cells, endogenous IMS-E21 (URLC8) expression was suppressed significantly by siRNA, and tRNA-DUS activity was reduced, resulted in suppression of growth of the cancer cells. The results herein suggest that IMS-E21 (URLC8) is likely to play an important role in synthesis of tRNA-dihydrouridine of NSCLC cells, being possibly essential for translation processes and, when over-expressed, for growth and survival of NSCLC cells. The data herein strongly imply the possibility of designing new anti-cancer drugs specifically inhibit IMS-E21 (URLC8). Targeting the IMS-E21 (URLC8) enzyme activity and/or the IMS-E21 (URLC8)-tRNA synthetase complex may be a promising therapeutic and diagnostic strategy for treatment of lung-cancer patients.

URLC8 and its Functional Equivalents and Uses thereof:

Herein, the words "a", "an", and "the" as used herein mean "at least one" unless otherwise specifically indicated.

As noted above, the present invention is based in part on the discovery of a novel t-RNA dihydrouridine-synthase, URLC8, which is involved in the proliferation of lung cancer cells. The present invention is also based on the finding that a high expression level of URLC8 is associated with poor prognosis in lung squamous-cell carcinoma (SCC) patients. In view of the evidence provided herein, that URLC8 expression is associated with poor prognosis of cancer patients, the present invention thus provides methods for determining a prognosis for cancer patients. An example of such a method comprises the steps of:

a. detecting a URLC8 expression level in a specimen collected from a subject whose SCC prognosis is to be predicted, and b. indicating a poor prognosis when an elevated level of URLC8 expression is detected.

In the context of the present invention, when the URLC8 expression level detected in a test specimen is higher than a control level, then the test specimen is deemed to have an elevated level of URLC8 expression. An example of a useful control level in the context of the present invention may comprise a standard value of URLC8 expression level taken from a group associated with good prognosis. The standard value may be obtained by any method known in the art. For example, a range of mean ±2 S.D. or mean ±3 S.D. may be used as the standard value. Alternatively, poor prognosis can be determined, when strong staining is observed by immunohistochemical analysis of sample tissue.

In the context of the present invention, an expression level of URLC8 may be detected by any one of the method selected from the group consisting of:
 (a) detecting an mRNA encoding the amino acid sequence of SEQ ID NO: 2,
 (b) detecting a protein comprising the amino acid sequence of SEQ ID NO: 2, and
 (c) detecting the biological activity of a protein comprising the amino acid sequence of SEQ ID NO: 2.

In the context of the present invention, the mRNA, the protein, or biological activity of the protein may be detected by any method. Methods for detecting a given protein, mRNA or biological activity thereof are well known to those skilled in the art. For example, mRNA may be detected using known PCR or hybridization based technologies. Alternatively, any immunoassay format may be applied for detection of a protein. Furthermore, the biological activity of URLC8, e.g. t-RNA dihydrouridine-synthase, or interactions between EPRS, may also detected using any suitable assay method, such as those described herein.

In the context of the present invention, determination of a poor prognosis may be used to determine further treatment, e.g., to stop further treatments that reduce quality of life, to treat the cancer in a different manner than previously used, or to treat the cancer more aggressively. In other words, the prediction of prognosis by URLC8 enables clinicians to choose in advance the most appropriate treatment for an individual SCC patient without even the information of conventional clinical staging of the disease, using only routine procedures for tissue-sampling.

Further, the methods of the present invention may be used to assess the efficacy of a course of treatment. For example, in a mammal with cancer from which a biological sample is found to have an elevated level of URLC8 expression, the efficacy of an anti-cancer treatment can be assessed by monitoring the URLC8 expression level over time. For example, a decrease in URLC8 expression level in a biological sample taken from a mammal following a course of treatment, as compared to a level observed in a sample taken from the mammal before treatment onset, or earlier in, the treatment, may be indicative of efficacious treatment.

As noted above, the present invention also provides kits for predicting lung squamous-cell carcinoma (SCC) prognosis, comprising any one component selected from the group consisting of:
 (a) a reagent for detecting an mRNA encoding the amino acid sequence of SEQ ID NO: 2,
 (b) a reagent for detecting a protein comprising the amino acid sequence of SEQ ID NO: 2, and
 (c) a reagent for detecting a biological activity of the protein comprising the amino acid sequence of SEQ ID NO: 2.

URLC8 has t-RNA dihydrouridine-synthase activity, and its expression level is markedly elevated in lung cancer cells as compared to non-lung cancer tissues. Thus, URLC8-mediated t-RNA dihydrouridine-synthase activity is useful as a diagnostic parameter of lung cancer, e.g. non-small cell lung cancer. Accordingly, the present invention provides a method of diagnosing non-small cell lung cancer or a predisposition to developing non-small cell lung cancer in a subject, comprising the step of determining a level of t-RNA dihydrouridine-synthase activity and/or t-RNA dihydrouridine in a biological sample derived from the subject, wherein an increase in said level, as compared to a normal control level, indicates that said subject suffers from or is at risk of developing non-small cell lung cancer. Accumulation of t-RNA dihydrouridine in a cell reflects the presence of t-RNA dihydrouridine-synthase activity. Thus, the cellular t-RNA dihydrouridine-synthase activity can be evaluated through the determination of t-RNA dihydrouridine in a cell. The t-RNA dihydrouridine may be determined by any method known in the art. For example, t-RNA dihydrouridine can be determined through colorimetric assay using N-phenyl-p-phenylenediamine and 2,3-butadione monoxime (Jacobson, M. and Hedgcoth, C. (1970) Anal Biochem, 34: 459-469.). In the present invention any sample derived from a patient to be diagnosed may be used. An example of a preferred sample for use in the context of the present invention is a lung tissue obtained by biopsy or surgical-resection.

The present invention also provides a kit for detection of t-RNA dihydrouridine-synthase of URLC8. Examples of components of such kits include, t-RNA having D-loop as substrate, e.g., t-RNA$^{Phe}$ or other t-RNAs (excluding t-RNA$^{Tyr}$ and t-RNA$^{Glu}$), an antibody that binds to URLC8, and a detectable label for detecting the antibody in a cell.

The URLC8 cDNA consists of 2,020 nucleotides that contain an open reading frame of 1,479 nucleotides as set forth in SEQ. ID. NO.: 1. The open reading frame encodes a 493-amino acid protein having amino acid sequence as set forth in SEQ. ID. NO.: 2. The amino acid sequence shows a 30% homology to S. cerevisiae Dus1 (dihydrouridine synthase 1), is member of UPF0034 (unclassified protein family 0034), and contains a conserved DSRM (double-strand RNA binding motif). S. cerevisiae Dus1 catalyses the reduction of the 5,6-double bond of a uridine residue on D-loop in tRNA (Xing, F., et al., (2002) RNA, 8: 370-381.). URLC8 localized mainly in cytoplasm and co-localized with ER-abundant protein PDI.

The present invention is also based on the finding that URLC8 has t-RNA dihydrouridine-synthase activity. To that end, one aspect of the invention involves identifying test compounds that regulate URLC8-mediated t-RNA dihydrouridine-synthase activity. Accordingly, the present invention provides novel methods for identifying compounds that slow or arrest the progression of, e.g., non-small cell lung cancer, by inhibiting URLC8-mediated t-RNA dihydrouridine-synthase activity.

The invention thus provides a method of screening for a compound that modulates URLC8 t-RNA dihydrouridine-synthase activity. The method is practiced by contacting a URLC8, or a functional equivalent thereof having t-RNA dihydrouridine-synthase activity, with one or more candidate compounds, and assaying t-RNA dihydrouridine-synthase activity of the contacted URLC8 or the functional equivalent. A compound that modulates t-RNA dihydrouridine-synthase activity of the URLC8 or functional equivalent is thereby identified.

In the context of the present invention, the term "functionally equivalent" means that the subject protein has t-RNA dihydrouridine-synthase activity. Whether or not a subject protein has the target activity can be determined in accordance with the present invention. For example, t-RNA dihydrouridine-synthase activity can be determined by incubating a polypeptide under conditions suitable for synthesis of t-RNA dihydrouridine and detecting the t-RNA dihydrouridine synthesis level.

Methods for preparing proteins functionally equivalent to a given protein are well known to those skilled in the art and include conventional methods of introducing mutations into the protein. For example, one skilled in the art can prepare proteins functionally equivalent to the human URLC8 protein by introducing an appropriate mutation in the amino acid sequence of the human URLC8 protein via site-directed mutagenesis (Hashimoto-Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W, and Fritz H J. (1987) Methods. Enzymol. 154, 350-367; Kunkel, T A (1985), Proc. Natl. Acad. Sci. USA. 82, 488-492; Kunkel (1991), Methods Enzymol. 204, 125-139). Amino acid mutations can occur in nature, too. The proteins suitable for use in the context present invention include those proteins having the amino acid sequences of the human URLC8 protein in which one or more amino acids are mutated, provided the resulting mutated proteins are functionally equivalent to the human URLC8 protein. The number of amino acids to be mutated in such a mutant is generally 25 amino acids or less, preferably 10 to 15 amino acids or less, more preferably 5 to 6 amino acids or less, and even more preferably 2 to 3 amino acids or less. To maintain t-RNA dihydrouridine-synthase activity, it is preferable to conserve the DSRM (double-strand RNA binding motif) in the amino acid sequence of the mutated protein.

Mutated or modified proteins, proteins having amino acid sequences modified by deleting, adding and/or replacing one or more amino acid residues of a certain amino acid sequence, are known to retain the original biological activity (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science (1984) 224, 1431-1433, Dalbadie-McFarland, G. et al., Proc. Natl. Acad. Sci. USA (1982) 79, 6409-6413).

The amino acid residue to be mutated is preferably mutated into a different amino acid in which the properties of the amino acid side-chain are conserved (a process known in the art as "conservative amino acid substitution"). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a protein to which one or more amino acids residues are added to the amino acid sequence of human URLC8 protein (SEQ ID NO: 2) is a fusion protein containing the human URLC8 protein. Fusion proteins suitable for use in the context of the present invention include, for example, fusions of the human URLC8 protein and other peptides or proteins. Fusion proteins can be made using techniques well known to those skilled in the art, for example by linking the DNA encoding the human URLC8 protein of the invention with DNA encoding other peptides or proteins, so that the frames match, inserting the fusion DNA into an expression vector and expressing it in a host. There is no restriction as to the peptides or proteins to be fused to the protein of the present invention.

Known peptides that can be used as peptides that are fused to the URLC8 protein include, for example, FLAG (Hopp, T. P. et al., (1988) Biotechnology 6, 1204-1210), 6xHis containing six His (histidine) residues, 10xHis, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding a protein of the present invention and expressing the fused DNA prepared.

An alternative method known in the art to isolate functional equivalent proteins is, for example, the method using a hybridization technique (Sambrook, J. et al., (1989) Molecular Cloning 2nd ed. 9.47-9.58, Cold Spring Harbor Lab. Press). One skilled in the art can readily isolate a DNA having high homology with a whole or part of the URLC8 DNA sequence (e.g., SEQ ID NO: 1) encoding the human URLC8 protein, and isolate functional equivalent proteins to the human URLC8 protein from the isolated DNA. The proteins used for the present invention include those that are encoded by DNA that hybridize with a whole or part of the DNA sequence encoding the human URLC8 protein and are functional equivalent to the human URLC8 protein. These proteins include mammal homologues corresponding to the protein derived from human or rat (for example, a protein encoded by a monkey, mouse, rabbit and bovine gene). In isolating a cDNA highly homologous to the DNA encoding the human URLC8 protein from animals, it is particularly preferable to use tissues from testis or lung cancer.

The conditions of hybridization for isolating a DNA encoding a protein functionally equivalent to the human URLC8 protein can be routinely selected by a person skilled in the art. For example, hybridization may be performed by conducting pre-hybridization at 68° C. for 30 min or longer using "Rapid-hyb buffer" (Amersham LIFE SCIENCE), adding a labeled probe, and warming at 68° C. for 1 hour or longer. The following washing step can be conducted, for example, for a low stringency condition. Exemplary low stringency conditions include, for example, 42° C., 2×SSC, 0.1% SDS, or preferably 50° C., 2×SSC, 0.1% SDS. More preferably, high stringency conditions are selected. Exemplary high stringency conditions include, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization. Selection of the factors necessary to achieve a requisite level of stringency constitutes routine optimization that is well within the purview of one skilled in the art.

In place of hybridization, a gene amplification method, for example, the polymerase chain reaction (PCR) method, can be utilized to isolate a DNA encoding a protein functionally equivalent to the human URLC8 protein, using a primer synthesized based on the sequence information of the DNA (SEQ ID NO: 1) encoding the human URLC8 protein (SEQ ID NO: 2).

Proteins that are functionally equivalent to the human URLC8 protein, encoded by the DNA isolated through the above hybridization techniques or gene amplification techniques, normally have a high homology to the amino acid sequence of the human URLC8 protein. In the context of the present invention, the term "high homology" refers to a homology of 40% or higher, preferably 60% or higher, more preferably 80% or higher, even more preferably 95% or higher. The homology of a protein can be determined by following the algorithm in "Wilbur, W. J. and Lipman, D. J. (1983) Proc. Natl. Acad. Sci. USA 80, 726-730".

A protein useful in the context of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of a human URLC8 protein (SEQ ID NO: 2), it is useful in the context of the present invention.

The proteins useful in the context of the present invention can be prepared as recombinant proteins or natural proteins, by methods well known to those skilled in the art. A recombinant protein can be prepared, for example, by inserting a DNA encoding a protein of the present invention (for example, the DNA comprising the nucleotide sequence of SEQ ID NO: 1) into an appropriate expression vector, introducing the vector into an appropriate host cell, obtaining the extract, and purifying the protein by subjecting the extract to chromatography, for example, ion exchange chromatography, reverse phase chromatography, gel filtration, or affinity chromatography utilizing a column to which antibodies against the protein of the present invention are fixed, or by combining more than one of aforementioned columns.

In addition, when a protein useful in the context of the present invention is expressed within host cells (for example, animal cells and $E.\ coli$) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions, other than the objective protein, by cutting with thrombin or factor-Xa as required.

A natural protein can be isolated by methods known to those skilled in the art, for example, by contacting an affinity column, in which antibodies binding to the URLC8 protein described below are bound, with the extract of tissues or cells expressing a protein of the present invention. The antibodies can be polyclonal antibodies or monoclonal antibodies.

In the present invention, t-RNA dihydrouridine-synthase activity of URLC8 or its functional equivalent can be determined by methods known in the art. For example, URLC8 and a substrate, e.g. tRNA having D-loop can be incubated with a hydrogen donor, under suitable assay conditions for t-RNA dihydrouridine synthesis. In the present invention, exemplary conditions for the synthesis of t-RNA dihydrouridine include the steps of contacting the substrate, hydrogen donor, with t-RNA dihydrouridine-synthase or sample, and incubating them. A tRNA$^{Phe}$ and reduced form of nicotinamide adenine dinucleotide (NADH) or nicotinamide adenine dinucleotide phosphate (NADPH) are examples of suitable substrates and hydrogen donors, respectively. Preferably, the substrate or hydrogen atom of the donor is labeled for tracing t-RNA dihydrouridine. Specifically, in the context of the present invention, a radio labeled tRNA is the preferred substrate. The reduced radio-labeled-tRNA (t-RNA dihydrouridine) may be detected by any suitable method. Increase of molecular mass of tRNA by addition of hydrogen atoms can be detected, for example by suitable chromatography, e.g. thin layer chromatography. For example, suitable conditions for t-RNA dihydrouridine synthesis are set forth below:

Reaction Mixture:
  100 mM Tris-HCl (pH 8.0),
  100 mM ammonium acetate,
  5 mM MgCl$_2$,
  2 mM DTT,
  0.1 mM EDTA,
  1 mM NADPH,
  1 mM NADH, and
  50,000 cpm of labeled transcript of tRNA (6 fmol)

The reaction mixture is mixed with a sample containing t-RNA dihydrouridine-synthase to be determined, and incubated for 30 min. at 30° C. In titration assays, extracts and purified proteins are preferably diluted in buffer containing 50 mM Tris-HCl, pH 8.0, 250 µg/mL bovine serum albumin, and 2 mM DTT. In some assays, 250 µM of flavin adenine dinucleotide (FAD) may also be included. Following the incubation, RNA is extracted from the mixture, and treated with P1 nuclease. Then nucleotides are resolved by thin layer chromatography using either cellulose plates developed in one dimension with solvent containing ammonium sulfate (74 g/100 mL H$_2$0, pH 3.5) :H$_2$O: isopropanol (80:18:2, v/v/v), or using PEI-cellulose plates developed in two dimensions with 1 M acetic acid, pH 3.5, for the first dimension, and in buffer containing 74 g ammonium sulfate/100 mL H$_2$0 (adjusted to pH 3.5 with H$_2$SO$_4$) for the second dimension (Bochner & Ames, (1982) J Biol Chem 257:9759-9769). In titration assays, 1 U of activity is defined as the amount of protein required to convert half of the tRNA.

Alternatively, t-RNA dihydrouridine-synthase activity of URLC8 can be estimated based on t-RNA dihydrouridine accumulation. t-RNA dihydrouridine can be detected by a colorimetric method. Furthermore, t-RNA dihydrouridine-synthase activity of URLC8 can be determined by consumed NADH and/or NADPH during the reaction. Suitable methods for determination of NADH and/or NADPH are well known to a person skilled in the art. Alternatively, following the reaction, either or both of tRNA and reduced tRNA can be detected with mass spectrometry, e.g. MALDI-TOF-MS.

Various low-throughput and high-throughput enzyme assay formats are known in the art and can be readily adapted for detection or measuring of the t-RNA dihydrouridine-synthase activity of URLC8. For high-throughput assays, the tRNA substrate is preferably immobilized on a solid support, such as a multi-well plate, slide or chip. Following the reaction, the reduced product (t-RNA dihydrouridine) can be detected on the solid support. Alternatively, the t-RNA dihydrouridine-synthase reaction can take place in solution, after which the t-RNA dihydrouridine can be immobilized on a solid support, and detected. In order to detect the reduction of tRNA, for example, H$^3$ labeled NADH and/or NADPH may be used as a hydrogen donor. The reduced product (t-RNA dihydrouridine) can be traced with radioactive H$^3$. To facilitate such assays, the solid support may be coated with streptavidin and the t-RNA labeled with biotin. The skilled person can determine suitable assay formats depending on the desired throughput capacity of the screen.

Any test compound, including, but not limited to, cell extracts, cell culture supernatant, products of fermenting microorganisms, extracts from marine organisms, plant extracts, purified or crude proteins, peptides, non-peptide compounds, synthetic micromolecular compounds and natural compounds, can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead, one-compound" library method and (5) synthetic library methods using affinity chromatography selection. The biological library methods using affinity chromatography selection are limited to peptide libraries, while the other four approaches are applicable to peptide, non-peptide oligomer or small molecule libraries of compounds (Lam (1997) Anticancer Drug Des. 12: 145). Examples of methods for the synthesis of molecular libraries can be found in the art (DeWitt et al. (1993) Proc. Natl. Acad. Sci. USA 90: 6909; Erb et al. (1994) Proc. Natl. Acad. Sci. USA 91: 11422; Zuckermann et al. (1994) J. Med. Chem. 37: 2678; Cho et al. (1993) Science 261: 1303; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233). Libraries of compounds may be presented in solution (see Houghten (1992) Bio/Techniques 13: 412) or on beads (Lam (1991) Nature 354: 82), chips (Fodor (1993) Nature 364: 555), bacteria (U.S. Pat. No. 5,223,409), spores (U.S. Pat. Nos. 5,571, 698; 5,403,484, and 5,223,409), plasmids (Cull et al. (1992) Proc. Natl. Acad. Sci. USA 89: 1865) or phage (Scott and Smith (1990) Science 249: 386; Devlin (1990) Science 249: 404; Cwirla et al. (1990) Proc. Natl. Acad. Sci. USA 87: 6378; Felici (1991) J. Mol. Biol. 222: 301; US Pat. Application 2002103360).

A compound isolated by the screening method of the present invention is a candidate for drugs that inhibit the t-RNA dihydrouridine-synthase activity of URLC8 and can be applied to the treatment or prevention of NSCLC.

Moreover, a compound in which a part of the structure of the compound inhibiting the t-RNA dihydrouridine-synthase activity of URLC8 is converted by addition, deletion and/or replacement are also included in the compounds obtainable by the screening method of the present invention.

Treating and Preventing Lung Cancer:

The present invention provides compositions for treating or preventing NSCLC comprising any of the compounds selected by the screening methods of the present invention.

When administrating a compound isolated by a method of the present invention as a pharmaceutical for humans and other mammals, such as mice, rats, guinea-pigs, rabbits, cats, dogs, sheep, pigs, cattle, monkeys, baboons, and chimpanzees, the isolated compound can be directly administered or, alternatively, can be formulated into a dosage form using conventional pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compound can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to form tablets and capsules include, for example, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, Gaultheria adenothrix oil and cherry. When the unit-dose form is a capsule, a liquid carrier, such as an oil, can also be further included in the above ingredients. Sterile composites for injections can be formulated following normal drug implementations using vehicles such as distilled water used for injections.

Physiological saline, glucose, and other isotonic liquids, including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80(TM) and HCO-50.

Sesame oil and soy-bean oil are examples of suitable oleaginous liquids and may be used in conjunction with benzyl benzoate or benzyl alcohol as solubilizers. They may be further formulated with a buffer, such as phosphate buffer or sodium acetate buffer; a pain-killer, such as procaine hydrochloride; a stabilizer, such as benzyl alcohol or phenol; and an anti-oxidant. The prepared injection may be filled into a suitable ampule.

Methods well known to those skilled in the art may be used to administer a pharmaceutical composition of the present invention to patients, for example, as intra-arterial, intravenous, or percutaneous injections and also as intranasal, transbronchial, intramuscular or oral administrations. The dosage and method of administration may vary according to the body-weight and age of the patient and the selected administration method; however, one skilled in the art can routinely select a suitable method of administration and dosage. If said compound is encodable by a DNA, the DNA can be inserted into a vector for gene therapy and the vector can be administered to a patient to perform the therapy. The dosage and method of administration may again vary according to the body-weight, age, and symptoms of the patient; however, one skilled in the art can suitably select them.

For example, although the dose of a compound that binds to URLC8 and regulates its activity depends on the symptoms, a suitable dose is generally about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

The present invention further provides a method for treating a NSCLC in a subject. Administration can be prophylactic or therapeutic to a subject at risk of (or susceptible to) a disorder or having a disorder associated with aberrant the t-RNA dihydrouridine-synthase activity of URLC8. The method includes decreasing the function of URLC8 in a non-small cell lung cancer (NSCLC) cell. Function can be inhibited through the administration of a compound obtained by the screening method of the present invention.

Also, an siRNA against a URLC8 gene can be used to reduce the expression level. Herein, term "siRNA" refers to a double stranded RNA molecule that prevents translation of a target mRNA. Standard techniques for introducing siRNA into a cell are used, including those in which DNA is a template from which siRNA is transcribed. In the context of the present invention, the siRNA comprises a sense nucleic acid sequence and an anti-sense nucleic acid sequence against URLC8. The siRNA method of the present invention can be used to alter the expression in a cell of an up-regulated NSCLC gene, e.g., up-regulation resulting from the malignant transformation of the cells. Binding of an siRNA to a transcript corresponding to URLC8 in a target cell results in a reduction in the protein production by the cell. The length of the oligonucleotide is preferably at least 10 nucleotides and may be as long as the naturally-occurring the transcript. Preferably, the oligonucleotide is about 19-25 nucleotides in length. More preferably, the oligonucleotide is less than 75, less than 50, or less than 25 nucleotides in length. Examples of URLC8 siRNA oligonucleotides which inhibited the expression in A549 and LC319cells include the target sequence containing SEQ ID NO: 11.

An siRNA of the present invention can be constructed such that a single transcript has both the sense and complementary antisense sequences from the target gene, e.g., as a hairpin.

An siRNA of URLC8 hybridizes to a target mRNA and thereby decreases or inhibits the production of URLC8 polypeptides by associating with the normally single-stranded mRNA transcript, thereby interfering with translation and thus, expression of the protein. In order to enhance the inhibition activity of an siRNA, nucleotide "u" can be added to 3' end of the antisense strand of the target sequence. The number of "u"s to be added is at least 2, generally 2 to 10, preferably 2 to 5. The added "u"s form single strand at the 3' end of the antisense strand of the siRNA.

An siRNA of URLC8 can be directly introduced into the cells in a form that is capable of binding to the mRNA transcripts. Alternatively, a DNA encoding the siRNA may be carried in a vector.

Vectors may be produced, for example, by cloning an URLC8 gene target sequence into an expression vector having operatively-linked regulatory sequences flanking the sequence in a manner that allows for expression (by transcription of the DNA molecule) of both strands (Lee, N. S., et al., (2002) Nature Biotechnology 20: 500-505.). An RNA molecule that is antisense to mRNA of URLC8 is transcribed by a first promoter (e.g., a promoter sequence 3' of the cloned DNA) and an RNA molecule that is the sense strand for the mRNA of URLC8 gene is transcribed by a second promoter (e.g., a promoter sequence 5' of the cloned DNA). The sense and antisense strands hybridize in vivo to generate siRNA constructs for silencing of the URLC8 gene. Alternatively, the two constructs can be utilized to create the sense and antisense strands of an siRNA construct. Cloned URLC8 gene can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence selected from the group consisting of nucleotides of SEQ ID NO: 11.

[B] is a ribonucleotide sequence consisting of 3 to 23 nucleotides, and

[A'] is a ribonucleotide sequence consisting of the complementary sequence of [A]. The region [A] hybridizes to [A'], and then a loop consisting of region [B] is formed. The loop sequence may be preferably 3 to 23 nucleotide in length. The loop sequence, for example, can be selected from group consisting of following sequences (http://www.ambion.com/techlib/tb/tb_506.html). Furthermore, loop sequence consisting of 23 nucleotides also provides active siRNA (Jacque, J. M., et al., (2002) Nature 418: 435-438.).

CCC, CCACC or CCACACC: Jacque, J. M, et al., (2002) Nature 418: 435-438.

UUCG: Lee, N. S., et al., (2002) Nature Biotechnology 20: 500-505. Fruscoloni, P., et al., (2003) Proc. Natl. Acad. Sci. USA 100: 1639-1644.

UUCAAGAGA: Dykxhoorn, D. M., (2003) Nature Reviews Molecular Cell Biology 4: 457-467.

Examples of preferred siRNAs having hairpin loop structure of the present invention are shown below. In the following structure, the loop sequence can be selected from group consisting of, CCC, UUCG, CCACC, CCACACC, and UUCAAGAGA The preferred loop sequence is UUCAAGAGA ("ftcaagaga" in DNA). Exemplary hairpin siRNA suitable for use in the context of the present invention include:
ugaggugcucagcacagug-[b]-cacugugcugagcaccuca (for target sequence of SEQ ID NO: 10)
guuggcacagccuguguau -[b]- auacacaggcugugccaac (for target sequence of SEQ ID NO: 11)

The regulatory sequences flanking the URLC8 genes can be identical or different, such that their expression can be modulated independently, or in a temporal or spatial manner. siRNAs are transcribed intracellularly by cloning the URLC8 gene template into a vector containing, e.g., a RNA polymerase III transcription unit from the small nuclear RNA (snRNA) U6 or the human Hi RNA promoter. For introducing the vector into the cell, transfection-enhancing agent can be used. FuGENE6 (Roche diagnostics), Lipofectamine 2000 (Invitrogen), Oligofectamine (Invitrogen), and Nucleofector (Wako pure Chemical) are useful as the transfection-enhancing agent.

The siRNA of the present invention inhibits the expression of a polypeptide of the invention and is thereby useful for suppressing the biological activity of the polypeptide of the invention. Also, expression-inhibitors, comprising siRNA of the present invention, are useful in that they can inhibit the biological activity of a polypeptide of the invention. Therefore, a composition comprising an antisense oligonucleotide of the present invention, such as an siRNA, is useful in treating NSCLC.

Thus, the present invention provides a composition for treating or preventing non-small cell lung cancer (NSCLC), comprising a pharmaceutically effective amount of small interfering RNA (siRNA) against a URLC8 gene, wherein said small interfering RNA comprises the nucleotide sequence 5'-TGAGGTGCTCAGCACAGTG-3' (SEQ ID NO: 10) and 5'-GTTGGCACAGCCTGTGTAT-3' (SEQ ID NO: 11) as the target sequence. Alternatively, the present invention further provides a method for treating or preventing NSCLC, said method comprising the step of administering a pharmaceutically effective amount of the small interfering RNA.

Patients with tumors characterized as over-expressing URLC8 may be treated by administering URLC8-siRNA. siRNA therapy is used to inhibit expression of URLC8 in patients suffering from or at risk of developing non-small cell lung cancer (NSCLC). Such patients are identified by standard methods of the particular tumor type; for example, non-small cell lung cancer (NSCLC) is typically diagnosed by tomography, ultrasound or biopsy.

Treatment is efficacious if the treatment leads to a clinical benefit, such as a reduction in the expression of URLC8, or a decrease in size, prevalence, or metastatic potential of the tumor in the subject. When treatment is applied prophylactically, "efficacious" means that the treatment retards or prevents tumors from forming or prevents or alleviates a clinical symptom of the tumor. Efficaciousness may be determined in association with any known method for diagnosing or treating the particular tumor type.

siRNA therapy is carried out by administering to a patient an siRNA using standard vectors and/or gene delivery systems. Suitable gene delivery systems may include liposomes, receptor-mediated delivery systems, and viral vectors, such as herpes viruses, retroviruses, adenoviruses and adeno-associated viruses, among others. A reduction in URLC8 production results in a decrease in URLC8 protein expression. A therapeutic nucleic acid composition is preferably formulated with a pharmaceutically acceptable carrier. The therapeutic composition may also include a gene delivery system as described above. Pharmaceutically acceptable carriers are biologically compatible vehicles which are suitable for administration to an animal, e.g., physiological saline. A therapeutically effective amount of a compound is an amount which is capable of producing a medically desirable result, such as reduced production of a URLC8 gene product, reduction of cell growth, e.g., proliferation, or reduction in tumor growth in a treated animal.

Parenteral administration, such as intravenous, subcutaneous, intramuscular, and intraperitoneal delivery routes, may be used to deliver URLC8-siRNA compositions.

Dosages for any one patient depends upon many factors, including the patient's size, body surface area, age, the particular nucleic acid to be administered, sex, time and route of administration, general health, and other drugs being administered concurrently. Suitable dosage for intravenous administration of nucleic acids ranges from approximately $10^6$ to $10^{22}$ copies of the polynucleotide.

The polynucleotides of the present invention may be administered by standard methods, such as by injection into the interstitial space of tissues such as muscles or skin, introduction into the circulation or into body cavities or by inhalation or insufflation. Polynucleotides are preferably injected or otherwise delivered to the animal in combination with a pharmaceutically acceptable liquid carrier, e.g., a liquid carrier, which is aqueous or partly aqueous. The polynucleotides of the present invention may also beassociated with a liposome (e.g., a cationic or anionic liposome). The polynucleotides of the present invention preferably include the genetic information necessary for expression by a target cell, such as promoters.

In another aspect, the present invention includes pharmaceutical, or therapeutic, compositions containing one or more therapeutic compounds described herein. Pharmaceutical formulations may include those suitable for oral, rectal, nasal, topical (including buccal and sub-lingual), vaginal or parenteral (including intramuscular, subcutaneous and intravenous) administration, or for administration by inhalation or insufflation. The formulations may, where appropriate, be conveniently presented in discrete dosage units and may be prepared by any of the methods conventional in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i. e., without a carrier. Tablets and capsules for oral administration may contain conventional excipients, such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form, such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), or preservatives. Furthermore, the tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example, sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers, such as cocoa butter or polyethylene glycol. Formulations for topical administration in the mouth, for example, buccally or sublingually, include lozenges, comprising the active ingredient in a flavored base, such as sucrose and acacia or tragacanth, and pastilles comprising the active ingredient in a base, such as gelatin and glycerin or sucrose and acacia. For intra-nasal administration, the compounds of the present invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation, the compounds of the present invention are conveniently delivered from an insufflator, nebulizer, pressurized pack or other convenient aerosol spray delivery means. Pressurized packs may comprise a suitable propellant, such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds of the present invention may take the form of a dry powder composition, for example a powder mix of the compound and a suitable powder base, such as lactose or starch. The powder composition may be presented in a unit dosage form, in for example, capsules, cartridges, gelatin or blister packs from which the powder may be administered with the aid of an inhalator or insufflators.

When desired, the above-described formulations, adapted to give sustained release of the active ingredient, may be employed. The pharmaceutical compositions of the present invention may also contain other active ingredients, such as antimicrobial agents, immunosuppressants or preservatives.

It should be understood that in addition to the ingredients particularly mentioned above, the formulations of the present invention may include other agents conventional in the art, having regard to the type of formulation in question; for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. In addition, the route of administration may vary depending upon the condition and its severity.

EXAMPLES

Example 1

Materials and Methods (a) Lung Cancer Cell Lines and Tissue Samples.

The 19 human NSCLC and 4 SCLC cell lines used in this study were as follows: lung ADC A427, A549, LC319, PC3, PC9, PC14, and NCI-H1373; bronchioloalveolar cell carcinomas (BAC) NCI-H1666 and NCI-H1781; lung adenosquamous carcinoma (ASC) NCI-H226 and NCI-H647; lung SCC RERF-LC-AI, SK-MES-1, EBC-1, LU61, NCI-H520, NCI-H1703, and NCI-H2170; a lung large-cell carcinoma (LCC) LX1; and SCLC DMS114, DMS273, SBC-3, and SBC-5. All cells were grown in monolayers in appropriate medium supplemented with 10% fetal calf serum (FCS) and were maintained at 37° C. in an atmosphere of humidified air with 5% $CO_2$. Human small airway epithelial cells, SAEC were grown in optimized medium (SAGM) purchased from Cambrex Bio Science Inc. (Walkersville, Md.).

Primary NSCLC samples, of which 22 were classified as ADCs, 14 as SCCs, and one as ASC, were originally obtained from 37 patients, with written informed consent, for a study described elsewhere (Kikuchi, T. et al. (2003) Oncogene, 22: 2192-2205.). An independent set of fourteen additional primary NSCLCs, including seven ADCs and seven SCCs, were obtained along with adjacent normal lung tissue samples from patients undergoing surgery.

A total of 292 NSCLC and adjacent normal lung tissue samples used for immunostaining on tissue microarray and additional statistical analysis were also obtained from patients who underwent surgery.

(b) Semi-quantitative RT-PCR analysis.

Total RNA was extracted from cultured cells and clinical tissues using the Trizol reagent (Life Technologies, Inc.) according to the manufacturer's protocol. Extracted RNAs and normal human tissue poly(A) RNAs were treated with DNase I (Nippon Gene) and were reverse-transcribed using oligo (dT) primer and SuperScript II reverse transcriptase (Invitrogen). Semi-quantitative RT-PCR experiments were carried out with the following synthesized gene-specific primers or with ACTB-specific primers as an internal control:

(c) IMS-E21 (URLC8).

The following primers were used to isolated IMS-E21 (URLC8):

```
5'-GACCACATCCAACAGTATTCG-3'      (SEQ ID NO.3)
and

5'-TGCCAGGACATCTAACTTCTG-3';     (SEQ ID NO.4)

ACTB,
5'-GAGGTGATAGCATTGCTTTCG-3'      (SEQ ID NO.5)
and

5'-CAAGTCAGTGTACAGGTAAGC-3'.     (SEQ ID NO.6)
```

PCR reactions were optimized for the number of cycles to ensure product intensity within the logarithmic phase of amplification.

(d) Northern-blot Analysis.

Human multiple-tissue blots (BD Biosciences Clontech) were hybridized with a $^{32}$P-labeled PCR product of IMS-E21 (URLC8). The cDNA probes of IMS-E21 (URLC8) were prepared by RT-PCR using primers with the same above. Pre-hybridization, hybridization, and washing were performed according to the supplier's recommendations. The blots were autoradiographed with intensifying BAS screens (BIO-RAD, Hercules, Calif.) at room temperature for 30 hours.

(e) Cloning of a Full-length IMS-E21 (URLC8) cDNA and DNA Sequencing.

Firstly, the IMS-E21 (URLC8) sequence was searched against the EST database by BLAST program and found to be highly homologous to an EST clone (FLJ20399, NM_017803). cDNA was generated from total RNA derived from 12 normal organ mixed sample by random priming using SuperScript II reverse transcriptase (Invitrogen) according to the manufacturer's instructions. RT-PCR product was cloned into the pcDNA3.1-myc-His vector (Invitrogen) and confirmed by sequencing.

(f) Generation of Anti-IMS-E21 (URLC8) Antibodies.

Plasmids expressing IMS-E21 (RLC8) (full length) that contain His-tagged epitope at the $NH_2$-terminal of the individual proteins were prepared using pET28 vector (Novagen, Madison, Wis.). The recombinant protein was expressed in *Escherichia coli*, BL21 codon-plus strain (Stratagene, LaJolla, Calif.), and purified using TALON resin (BD Bioscience) according to the supplier's protocol. The protein extracted in SDS-PAGE gel was inoculated into rabbits, and the immune sera were purified on affinity columns according to the standard methodology. Affinity-purified anti-IMS-E21 (URLC8) antibodies were used for western-blot analysis, immunoprecipitation, and immunostaining.

(g) Co-immunoprecipitation and MALDI-TOF-MS Mapping of IMS-E21 (URLC8)-associated Proteins.

Cell extracts from lung-cancer cell line LC319 transfected with the plasmids expressing N-terminal FLAG-tagged and C-terminal HA-tagged-pCAGGS-IMS-E21 (URLC8) vector or mock vector (control) were pre-cleared by incubation at 4° C. for 1 hour with 100 μL of protein G-agarose beads in a final volume of 2 ml of IP-buffer (0.5% NP-40, 50 mM Tris-HCl, 150 mM NaCl) in the presence of proteinase inhibitor. After centrifugation at 1000 rpm for 5 min at 4° C., the supernatant was incubated at 4° C. with anti-Flag M2 agarose for 2 hours.

The beads were then collected by centrifugation at 5000 rpm for 2 min and washed six times with 1 ml of each immunoprecipitation buffer. Then, the washed beads were eluted by Flag-peptide (Sigma-Aldrich Co., St. Louis, Mo.). The elution was incubated at 4° C. with anti-HA agarose for 2 hours. The washed beads were resuspended in 50 μL of Laemmli sample buffer and boiled for 5 min, and the proteins were separated by 5-10% SDS PAGE gels (BIO RAD). After electrophoresis, the gels were stained with silver. Protein bands specifically found in IMS-E21 (URLC8)-transfected extracts were excised and served for matrix-assisted laser desorption/ ionization-time of flight mass spectrometry (MALDI-TOF-MS) analysis (AXIMA-CFR plus, SHIMADZU BIOTECH, Kyoto, Japan).

(h) RNA Interference Assay.

A vector-based RNA interference (RNAi) system, psiH1BX3.0, was previously established to direct the synthesis of siRNAs in mammalian cells (Suzuld, C. et al. (2003) Cancer Res, 63: 7038-7041.). Herein, 10 μg of siRNA-expression vector were transfected, using 30 μl of Lipofectamine 2000 (Invitrogen), into NSCLC cell lines A549 and LC319, both of which over-expressed IMS-E21 (URLC8) endogenously. More than 80% of the transfected cells expressed the synthetic siRNA, and in those cells endogenous expression of the IMS-E21 (URLC8) genes was effectively suppressed. The transfected cells were cultured for seven days in the presence of appropriate concentrations of geneticin (G418), after which cell numbers and viability were measured by Giemsa staining and triplicate MTT assays. The target sequences of the synthetic oligonucleotides for RNAi were as follows:

control 1 (EGFP: enhanced green fluorescent protein (GFP) gene, a mutant of *Aequorea victoria* GFP),

5'-GAAGCAGCACGACTTCTTC-3';    (SEQ ID NO.7)

control 2 (Luciferase: *Photinus pyralis* luciferase gene),

5'-CGTACGCGGAATACTTCGA-3';    (SEQ ID NO.8)

control 3 (Scramble: chloroplast *Euglena gracilis* gene coding for 5S and 16S rRNAs),

5'-GCGCGCTTTGTAGGATTCG-3';    (SEQ ID NO.9)

siRNA-IMS-E21-#2 (si-IMS-E21-#2),

5'-TGAGGTGCTCAGCACAGTG-3';    (SEQ ID NO.10)

siRNA-IMS-E21-#3 (si-IMS-E21-#3),

5'-GTTGGCACAGCCTGTGTAT-3'.    (SEQ ID NO.11)

The insert sequences of siRNA expression vectors were as follows:

control 1 (EGFP);

(SEQ ID NO.12)
5'-TCCCGAAGCAGCACGACTTCTTCTTCAAGAGAGAAGAAGTCGTGCTG
CTTC-3';

(SEQ ID NO.13)
5'-AAAAGAAGCAGCACGACTTCTTCTCTCTTGAAGAAGAAGTCGTGCTG
CTTC-3';

control 2 (Luciferase);

(SEQ ID NO.15)
5'-TCCCCGTACGCGGAATACTTCGATTCAAGAGATCGAAGTATTCCGCG
TACG-3';

(SEQ ID NO.16)
5'-AAAACGTACGCGGAATACTTCGATCTCTTGAAATCGAAGTATTCCGC
GTACG-3';

control 3 (Scramble);

(SEQ ID NO.18)
5'-TCCCGCGCGCTTTGTAGGATTCGTTCAAGAGACGAATCCTACAAAGC
GCGC-3';

(SEQ ID NO.19)
5'-AAAAGCGCGCTTTGTAGGATTCGTCTCTTGAACGAATCCTACAAAGC
GCGC-3';

siRNA-IMS-E21-#2 (si-IMS-E21-#2);

(SEQ ID NO.21)
5'-TCCCTGAGGTGCTCAGCACAGTGTTCAAGAGACACTGTGCTGAGCAC
CTCA-3';

(SEQ ID NO.22)
5'-AAAATGAGGTGCTCAGCACAGTGTCTCTTGAACACTGTGCTGAGCAC
CTCA-3';

siRNA-IMS-E21-#3 (si-IMS-E21-#3);

(SEQ ID NO.24)
5'-TCCCGTTGGCACAGCCTGTGTATTCAAGAGAATACACAGGCTGTGCC
AAC-3';

(SEQ ID NO.25)
5'-AAAAGTTGGCACAGCCTGTGTATCTCTTGAAATACACAGGCTGTGCC
AAC-3';

(i) Immunohistochemistry and Tissue Microarray Analysis.

The tumor tissue microarrays using formalin-fixed NSCLCs were constructed as published elsewhere. The tissue area for sampling was selected based on a visual alignment with the corresponding HE-stained section on a slide. Three, four, or five tissue cores (diameter 0.6 mm; height 3-4 mm) taken from the donor tumor blocks were placed into a recipient paraffin block using a tissue microarrayer (Beecher Instruments, Sun Prairie, Wis.). A core of normal tissue was punched from each case. 5-μm sections of the resulting microarray block were used for immunohistochemical analysis. IMS-E21 (URLC8) positivity were assessed semi-quantitatively, recording staining intensity as absent (scored as 0), weak (scored as 1+) or strongly positive (scored as 2+), by three independent investigators without prior knowledge of the clinical follow-up data. Cases were accepted only as positive if reviewers independently defined them thus.

To investigate the presence of IMS-E21 (URLC8) protein in clinical tissue samples, the sections were stained using ENVISION+Kit/HRP (DakoCytomation). Affinity-purified anti-IMS-E21 (URLC8) antibody was added after blocking endogenous peroxidase and proteins, and the sections were incubated with HRP-labeled anti-rabbit IgG as the secondary antibody. Substrate-chromogen was added and the specimens were counterstained with hematoxylin.

Example 2

Figure 1:
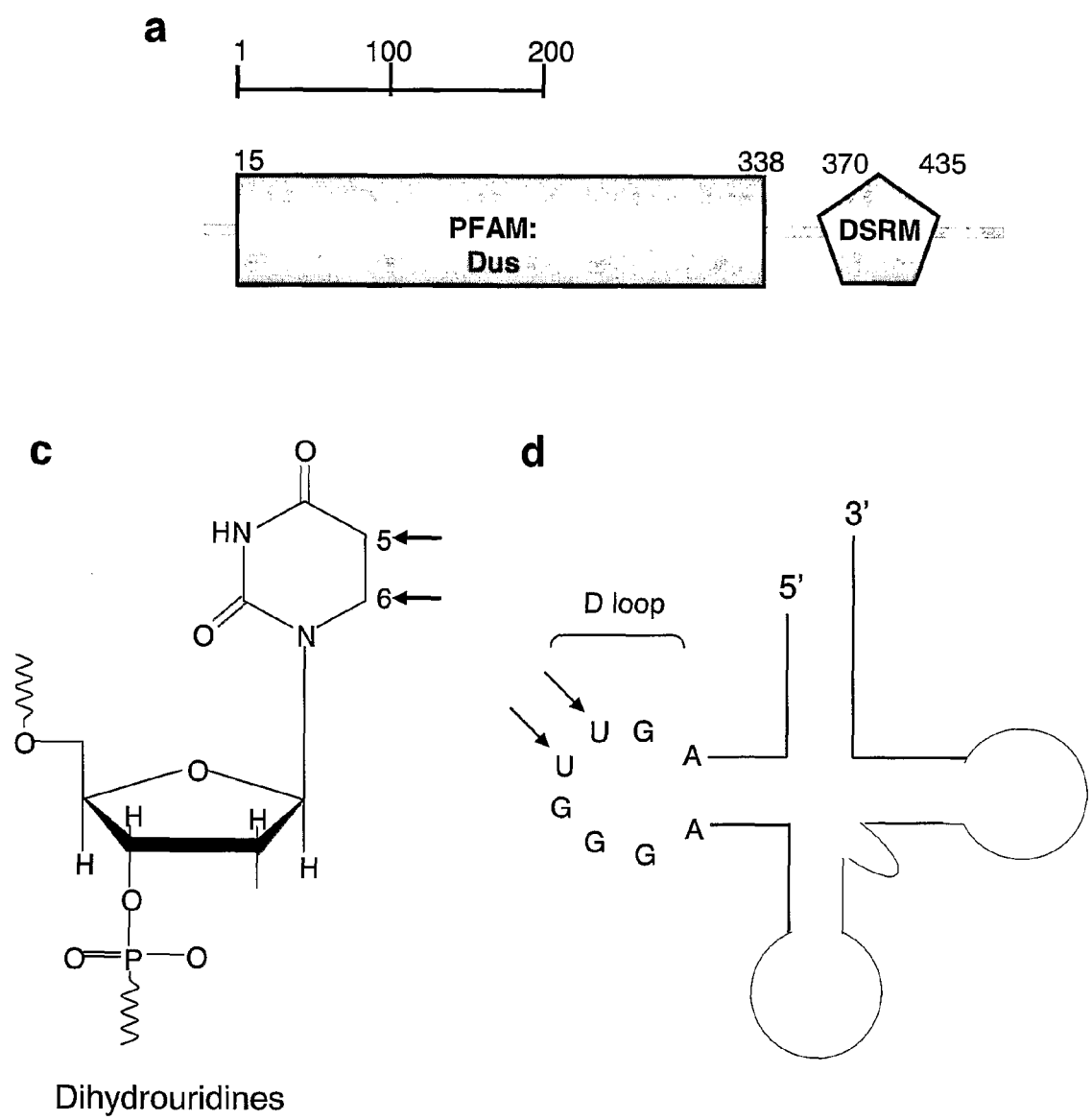
FIG. 1 depicts the structure of IMS-E21 (URLC8) and structural features of tRNA-dihydrouridine.

Cloning of IMS-E21 (URLC8) Gene and its Expression in Lung Tumors, Cell Lines, and Normal Tissues To obtain novel target molecules for development of therapeutic agents and/or diagnostic markers for NSCLC, genes that showed 5-fold higher expression in more than 50% of 37 NSCLCs analyzed by cDNA microarray (Kikuchi, et. al. (2003) Oncogene, 22: 2192-2205.) were screened. Among 23,040 genes screened, one EST transcript (FLJ20399, NM_017803) was identified as frequently over-expressed in NSCLCs; its overexpression was confirmed -in eight representative cases by semi-quantitative RT-PCR experiments. To obtain a full-length clone of this transcript, the FASTA database was screened using the cDNA fragment originally isolated by cDNA microarray experiment and identified several ESTs. Assembling DNA sequences of these clones, the entire coding nucleotide sequence of this gene was determined. The cDNA consisted of 2,020 nucleotides, including an open reading frame of 1,479 nucleotides that encoded a 493 amino acid peptide. A homology search using the FASTA program revealed that this predicted protein was homologous to proteins belonging to the family of tRNA-dihydrouridine synthase (DUS), especially *S. cerevisiae* Dus1 (dihydrouridine synthase 1) which catalyses the reduction of the 5,6-double bond of a uridine residue on tRNA (30% identity in amino acids, respectively; FIG. 1, *a-c*). Hence, this gene was tentatively designated IMS-E21 (also referred to as URLC8: upregulated in lung cancer 8, Accession No. AB101210). Two motifs were identified using SMART program (http://smart-.embl-heidelberg.de/) (Letunic I, et al., (2004) Nucleic Acids Res.; 32(Database issue):D142-4; Schultz J, et al., (1998) Proc Natl Acad Sci USA.; 95:5857-64.) within the sequence of IMS-E21 (URLC8); N-terminal Dus domain and C-terminal DSRM, respectively (FIG. 1, *a*). The human IMS-E21 (URLC8) (SEQ ID NO: 2) appeared to conserve 90% identity in amino acids with the murine (*M. musculus* and *R. Norvegicus* SEQ ID NOS: 27 and 28) products, 48% with the *D. melanogaster* protein (SEQ ID NO: 29), and 40% with *C. elegans* protein (SEQ ID NO: 30) (FIG. 1, *b*).

Increased IMS-E21 (URLC8) expression was further confirmed in 11 of 14 additional NSCLC cases (4 of 7 adenocarcinomas (ADCs); 7 of 7 squamous-cell carcinomas (SCCs) (FIG. 2, *a*), and documented up-regulation of IMS-E21 (URLC8) in 21 of the 23 NSCLC and small-cell lung cancer (SCLC) cell lines examined, but no expression was found in SAEC cells derived from normal bronchial epithelium (FIG. 2, *b*).

Northern blotting with IMS-E21 (URLC8) cDNA as a probe identified a 2.4-kb transcript as a band, mainly seen in testis, among the 23 normal human tissues examined (FIG. 2, *c*).

Example 3

Overexpression of IMS-E21 (URLC8) Protein is Associated with a Worse Outcome in SCC Immunohistochemical analysis was performed with affinity-purified anti-IMS-E21 (URLC8) polyclonal antibodies in tissue microarrays of available 292 NSCLCs. The study showed that the number of cases that showed positive staining of IMS-E21 (URLC8) in the cytoplasm was 254 of 292 (87%) NSCLC total cases; 132 of 158 (84%) ADC cases, 89 of 99 (90%) SCC cases, 19of 21 (90%) LCC cases, 10 of 10 (100%) BAC cases, and 4of 4 (100%) ASC cases, respectively. All of those tumors were surgically-resectable NSCLCs, and no staining was observed in any of their adjacent normal lung tissues (FIG. 3, *a*). A pattern of IMS-E21 (URLC8) expression was classified on the tissue array, ranging from absent/weak (scored as 0~1+) to strong (scored as 2+). Next, the association of IMS-E21 (URLC8) expression with clinical outcome was examined. Statistical analysis revealed no significant correlation of any levels of IMS-E21 (URLC8) expression with pT- or pN- factors among the lung-cancer patients examined. However, the expression of IMS-E21 (URLC8) in SCC was found to be significantly associated with tumor specific 5 year-survival using Kaplan-Meier method (P=0.0091 by the Log-rank test) (FIG. 3, *b*). By univariate analysis pT, pN, gender, and IMS-E21 (URLC8) expression (P=0.0111) were each significantly related to a poor tumor-specific survival among SCC patients. Furthermore, IMS-E21 (URLC8) staining was determined to be an independent prognostic factors by multivariate analysis using Cox proportional hazard model of SCC patients (P=0.0234).

Example 4

Inhibition of Growth of NSCLC Cells by Specific siRNA Against IMS-E21 (URLC8)

To assess whether IMS-E21 (URLC8) is essential for growth or survival of lung-cancer cells, plasmids were designed and constructed to express siRNA against IMS-E21 (URLC8) (si-IMS-E21) and control plasmids (siRNAs for EGFP, Scramble, and Luciferase) and transfected them into A549 and LC319cells to suppress expression of endogenous IMS-E21 (URLC8). The amount of IMS-E21 (URLC8) transcript and protein level in the cells transfected with si-IMS-E21-#2, and -#3 were significantly decreased in comparison with cells transfected with the control (FIG. 3, *c*, left panels); transfection of si-IMS-E21-#2, and -#3 also resulted in significant decreases of colony number in colony-formation assays (FIG. 3, *c*, lower panels) and colony numbers measured by MTT cell viability assay (FIG. 3, *c*, right panel).

Example 5

IMS-E21 (URLC8) Localized Mainly in Cytoplasm and Co-localized with ER-abundant Protein PDI To determine the subcellular localization of endogenous IMS-E21 (URLC8) in lung cancer-cells, immunocytochemistry was performed using affinity-purified anti-IMS-E21 (URLC8) polyclonal antibodies. Confocal microscopy revealed the distribution of the IMS-E21 (URLC8) protein in the cytoplasm of A549 cells (data not shown). To further investigate the sub-cellular localization of IMS-E21 (URLC8) proteins, we transfected LC319 cells with plasmids that contained c-myc-His-epitope sequences (LDEESI-LKQE-HHHHHH; SEQ ID NO: 33) at the C-terminal of the human IMS-E21 (URLC8) protein. Co-immunostaining using anti-c-myc antibodies and antibodies against endogenous Protein Disulfide Isomerase (PDI), which are abundantly expressed in endoplasmic reticulum (ER) suggested that IMS-E21 (URLC8) protein mainly distribute at ER (FIG. 4, a).

Example 6

Identification of EPRS as a Protein Interacting with IMS-E21 (URLC8)

To elucidate the function of IMS-E21 (URLC8) in lung-cancer cells, protein(s) interacting with IMS-E21 (URLC8) were identified. Lysate of LC319 cells transfected with N-terminal FLAG-tagged and C-terminal HA-tagged-pCAGGS-IMS-E21 vector or mock vector (control) were extracted and immunoprecipitated with anti-FLAG M2 monoclonal antibody followed by immunoprecipitation with anti-HA monoclonal antibody. The protein complex including IMS-E21 (URLC8) was stained with SilverQuest (Invitrogen) on the SDS-PAGE gel. A 180-kDa band, which was seen in immunoprecipitates of cell lysates transfected with IMS-E21 (URLC8) expressing plasmids, but not seen in those with mock plasmids was extracted and determined to be EPRS (glutamyl-prolyl tRNA synthetase), by MALDI-TOF mass spectrometric sequencing (data not shown). The interaction between endogenous IMS-E21 (URLC8) and EPRS was confirmed by co-immunoprecipitation and immunocytochemistry (FIG. 4, b and c), suggesting the possibility of existence of IMS-E21 (URLC8)-aminoacyl tRNA synthetase complex in an ER-dependent translation.

Example 7 tRNA-DUS Activity of IMS-E21 (URLC8) in Lung Cancer Cells

To test the hypothesis that IMS-E21 (URLC8) encodes a family of dihydrouridine synthase enzyme, the effects of suppression of IMS-E21 (URLC8) gene by siRNA on DUS activity in NSCLC cell line were investigated. Total tRNA was purified from total RNA of A549 and LC319 cells transfected with siRNA constructs by HPLC technique and analyzed the samples for dihydrouridine content of each cell line(Jacobson, M. and Hedgcoth, C. (1970) Anal Biochem, 34: 459-469. Hunninghake, D. and Grisolia, S. (1966) Anal Biochem, 16: 200-205.). Most effective IMS-E21 (URLC8) siRNA constructs (si-IMS-E21-#2), which could suppress transcript levels of IMS-E21 (URLC8) as stated above, also lead to reduce levels of tRNA-dihydrouridine content when compared with their corresponding control siRNA construct (si-EGFP) (FIG. 4, d). The deficiencies of tRNA-dihydrouridine induced by si-IMS-E21-#2 in these tumor cells were closely related to the tumor growth suppression (FIG. 3, c), implicating that tRNA-DUS activity of IMS-E21 (URLC8) is indispensable for tumor cell survival and/or progression.

INDUSTRIAL APPLICABILITY

The present inventors have shown that URLC8 has t-RNA dihydrouridine-synthase activity, and the suppression of the activity leads to the inhibition of cell proliferation of lung cancer cells. Thus, agents that inhibit the t-RNA dihydrouridine-synthase activity of URLC8 find therapeutic utility as anti-cancer agents for the treatment of lung cancer, such as NSCLC.

In addition, treatment of NSCLC cells with siRNA against URLC8 suppressed its expression and also the activity of tRNA-DUS, and suppressed growth of the cancer cells. Additional experiments revealed that the URLC8 protein physically interacts with EPRS (glutamyl-prolyl tRNA synthetase) in NSCLC cells. These data imply that up-regulation of URLC8 function and increased tRNA-DUS activity are common features of pulmonary carcinogenesis. Accordingly, the selective suppression of URLC8 enzyme activity and/or the formation of the URLC8-tRNA synthetase complex may be a promising therapeutic strategy for treatment of lung-cancer patients.

Alternatively, lung cancer can be detected using t-RNA dihydrouridine-synthase activity of URLC8 as a diagnostic index.

Furthermore, the present inventors revealed that a high level of URLC8 (IMS-E21) expression was significantly associated with poor prognosis for patients with lung squamous-cell carcinoma (SCC). Accordingly, a prognosis of lung cancer can be predicted by measurement of URLC8 (IMS-E21) expression level.

All patents, patent applications, and publications cited herein are incorporated by reference in their entirety. Furthermore, while the invention has been described in detail and with reference to specific embodiments thereof, it will be apparent to one skilled in the art that various changes and modifications can be made therein without departing from the spirit and scope of the invention.

The invention claimed is:

1. A method of predicting a lung squamous-cell carcinoma (SCC) prognosis, wherein the method comprises the steps of:
   a. detecting expression level of a URLC8 protein comprising the amino acid sequence of SEQ ID NO: 2 in a specimen collected from a subject whose SCC prognosis is to be predicted, and
   b. indicating a poor prognosis when an elevated URLC8 expression level, as compared to a control level, is detected.

* * * * *